United States Patent [19]
Morrison et al.

[11] Patent Number: 5,827,531
[45] Date of Patent: Oct. 27, 1998

[54] MICROCAPSULES AND METHODS FOR MAKING

[75] Inventors: Dennis R. Morrison, Kemah; Benjamin Mosier, Houston, both of Tex.

[73] Assignee: The United States of America as represented by the Administrator of the National Aeronautics and Space Administration, Washington, D.C.

[21] Appl. No.: 349,169

[22] Filed: Dec. 2, 1994

[51] Int. Cl.[6] .................................. A61K 9/50; A61K 9/52
[52] U.S. Cl. ........................ 424/450; 424/451; 424/489; 424/490; 427/213.3; 428/402.21; 428/402.24; 264/4.32; 264/4.33
[58] Field of Search ................................ 424/450, 1, 489, 424/490; 427/213.3; 428/402.21, 402.24; 264/4.32, 4.33

[56] References Cited

U.S. PATENT DOCUMENTS

| | | | |
|---|---|---|---|
| 3,639,306 | 2/1972 | Sternberg et al. | 260/2.5 B |
| 4,492,720 | 1/1985 | Mosier | 427/213.3 |
| 4,501,728 | 2/1985 | Geho et al. | 424/38 |
| 4,855,090 | 8/1989 | Wallach | 264/4.1 |
| 4,909,933 | 3/1990 | Carter et al. | 210/95 |
| 5,013,556 | 5/1991 | Woodle et al. | 424/450 |
| 5,032,457 | 7/1991 | Wallach | 428/402.2 |
| 5,192,549 | 3/1993 | Barenolz et al. | 424/450 |
| 5,192,551 | 3/1993 | Willoughby, Jr. et al. | 424/489 |
| 5,225,212 | 7/1993 | Martin et al. | 424/450 |

OTHER PUBLICATIONS

Allen, TM., Interactions of Liposomes and other Drug Carriers with the Mononuclear Phagocyte System, in G. Gregoriadis (Ed.) *Liposomes as Drug Carriers*, John Wiley & Sons Ltd., New York, pp. 37–50, 1988.

Allen, T.M., Mehra, T., Hansen, C. and Chin, Y.C., Stealth Liposomes: An Improved Sustained Release System for 1–β–D–Arabinofuranosylcytosine, Cancer Res. 52:2431–39, 1992.

Bhargava, H. N., Narurkar, A., & Lieb, L. M., Using Micromulsions for Drug Delivery, Pharmaceutical Technology, pp. 46, 48, 50, 52 & –54; Mar. 1987.

Gabizon, A., et al., Liposome–Associated Doxorubicin: Pre-clinical Pharmacology and Exploratory Clincial Phase, In G. Lopen–Berestein and I.J. Fidler (Eds.) *Therapy of Infectious Diseases and Cancer*, Alan R. Liss, Inc., New York, pp. 391–402, 1989.

(List continued on next page.)

*Primary Examiner*—Thurman K. Page
*Assistant Examiner*—James M. Spear
*Attorney, Agent, or Firm*—James M. Cate

[57] ABSTRACT

Methods of forming multi-lamellar microcapsules having alternating layers of hydrophilic and hydrophobic immiscible liquid phases have been developed using different polymer/solvent systems. The methods use liquid-liquid diffusion and simultaneous lateral phase separation, controlled by proper timed-sequence exposures of immiscible phases and low shear mixing, to form narrow size distributions of spherical, multilamellar microcapsules. The use of special formulations of solubilized drugs, surfactants, and polymeric co-surfactants in aqueous vehicles which are dispersed in hydrocarbon solvents containing small quantities of oil, low molecular weight co-surfactants and glycerides that are aqueous insoluble enables the formation of unique microcapsules which can carry large amounts of pharmaceuticals in both aqueous and non-aqueous solvent compartments. The liquid microcapsules are quickly formed in a single step and can include a polymeric outer "skin" which protects the microcapsules during physical manipulation or exposure to high shear forces. Water-in-oil and oil-in-water microcapsules have been formed both in 1×g and in microgravity, which contain several types of drugs co-encapsulated within different fluid compartments inside the same microcapsule. Large, spherical multi-lamellar microcapsules have been formed including a cytotoxic drug co-encapsulated with a radiocontrast medium which has advantages for chemoembolization of vascular tumors. In certain cases, crystals of the drug form inside the microcapsules providing zero-order and first order, sustained drug release kinetics.

84 Claims, 6 Drawing Sheets

OTHER PUBLICATIONS

Halbert, G.W., Stuart, J.F.B., Florence, A. T., The Incorporation of Lipid Soluble Antineoplastic Agents into Microemulsions–Protein–free Analogues of Low Density Lipoprotein, Int. J. Pharm. 21:219–232., 1984.

Kimler, B. F. et al., Combination of Aziridinylbenzoquinone and Cis–platinum with Radiation Therapy in the 9L Rat Brain Tumor Model, Int. J. Radiation Oncology Biol. Phys, 26: 445–450, 1993.

McCutcheon's Detergents and Emulsifiers, 1979, North American Edicition, McCutcheon Division, MC Publishing Co., 175 Rock Road, Glen Rock, NJ 07452.

Parikl, I, & Stern, W., Microcrystal™ Drug Delivery System, in Harvey S. Price (Ed) *The Biotechnology Report* 1993/94, Bookbuilders, Ltd., Hong Kong, pp. 219–220, 1994.

Talsuma, H. and Crommelin, D. J. A., Liposomes as Drug Delivery Systems, Part 1: Preparation. Pharaceutical Technology, pp. 96, 98, 100, 102, 104, & 106, Oct. 1992.

Wright, K. C., Wallace, S., Mosier, B., & Mosier, D., Microcapsules for Arterial Chemoembolization: Appearance and In Vitro Drug Release Characteristics, J. Microencapsulation, vol 5 #1, pp. 13–20, 1988.

MICROCAPSULES AND METHODS FOR MAKING

ORIGIN OF THE INVENTION

The invention described herein may be manufactured and used by or for the Government of the United States of America for governmental purposes without the payment of any royalties thereon or therefor.

BACKGROUND OF THE INVENTION

A. Field of the Invention

The invention relates to methods for making microcapsules, encapsulating pharmaceutical compounds in microcapsules, microcapsules, microcapsule encapsulated pharmaceutical compositions and products, and methods of using the same.

B. Description of the Related Art

Many cytotoxic or bioactive drugs and enzymes cannot be injected intravenously. Others can be injected, but are rapidly degraded before they reach the target tissue. Still others are cleared from the blood by the liver or kidneys so quickly that their biological half-life is too short to be of therapeutic value. Still other drugs are insoluble in aqueous solutions. Since intravenous injection in hydrocarbon solvents is not well tolerated by patients, such drugs are difficult to administer.

One method for overcoming these limitations is encapsulation into microcapsules or liposomes. Encapsulation of drugs or biological therapeutics into liposomes or liquid microcapsules can enable delivery to target organs where the bioactive drug can be released directly by diffusion. Properly designed microcapsules can provide unique methods of direct delivery by parenteral injection, nasal inhalation and dermal administration for sustained release of important bioactive drugs.

The size and shape of the microcapsules is critical for the distribution and drug delivery in the tissues. Typically, microcapsules of 1–20 micron diameter are optimum for intravenous administration, whereas, 50–300 micron diameter microcapsules are used for intraarterial delivery and 300 micron or greater for intraperitoneal administration. In each size range, highly uniform microspheres are needed for maximum packing densities and maximum drug payload delivery to target organs or tumors.

Major difficulties with commercial preparation of microspheres arise when density-driven phase separation of the immiscible carrier fluids occurs. This is especially true when the microcapsules are constructed by forming water/oil emulsions or when attempts are made to encapsulate multiple drugs. This limits the yield and often results in microparticles that are not spherical nor uniform in size. Nonconformity limits the packing density (and, thereby, the drug payload delivered) when the microcapsules arrive at the target tissues.

Certain current methods of forming microcapsules (such as liposomes) are based on chemical characteristics of certain phospholipids that self-assemble into bilayers when dispersed in an excess of water. Most liposomes carry pharmaceuticals dissolved in the entrapped water phase. Drugs that are insoluble or that have only limited solubility in aqueous solvents pose problems for incorporating into liposomes. Such organic-soluble drugs are usually limited in liposomal formulations to those that bind inside the hydrophobic region of the liposome bilayer. Some drugs are so insoluble that they do not associate with the bilayer and, therefore, have very low encapsulation efficiencies. Certain liposomal drug formulations, including anti-tumor liposomes containing dexorubicin [Gabizion et al. 1992] or muramyltripeptide have been studied extensively in clinical trials.

Microcapsule formation by liquid-liquid dispersion of aqueous drugs and organic solvents typically produces water-in-oil (W/O) type liposomes. A second requisite step is removal of the organic solvent (typically evaporated) to form reverse-phase evaporation vesicles (rev) or stable plurilamellar vesicles (splv).

Spherical multilamellar vesicles (mlv) are rarely formed by these methods and the size distribution is quite heterogeneous. Typically, in order to generate multilamellar vesicles, film casting with organic solvents, hydration and sizing using filtration through inert membrane filters is required [Talsma and Crommelin 1992]. Methods of forming multi-layered microcapsules often require emulsification of the aqueous phase into organic carrier solutions by shear, bubbling or sonication. Sophisticated, multi-step emulsion technology is required and yields of uniform type and size are often very low.

Liquid microemulsions also have been developed as drug delivery systems, especially for drugs that are poorly soluble in aqueous carriers. A microemulsion typically contains droplets in the range of 0.1–1$\mu$ in diameter. Such microemulsions are characterized by very fluid and dynamic micelles which are formed by sequential mixing one immiscible phase with another using surfactants and co-surfactants [Bhargava et al. 1987]. Typically, surfactants that produce water-in-oil (W/O) microemulsions have a hydrophilic-lipophilic balance (HLB) rating of 3 to 6, while those that produce oil-in-water (O/W) microemulsions have an HLB of 8 to 18. The surfactants can be non-ionic, ionic, or amphoteric. Often, medium chain-length alcohols are added as the co-surfactant in the last step in achieving the final microemulsion.

The major disadvantages of microemulsions is that each micelle (liquid capsule) is too small (typically, less than 1.0 micron) for deposition in larger vascular beds when administered by intravascular injection. Therefore, microemulsions are not suitable for chemoembolization type treatment of vascularized tumors. Additionally, since microemulsions are true colloidal suspensions, they cannot be scaled up to large enough size for many intravascular drug delivery applications. Microemulsions formed with lipid soluble antitumor agents and low density lipoproteins (LDLS) have been used to target drugs to neoplastic cells that require large amounts of cholesterol for synthesis of cell membranes [Halbert et al. 1984]. However, LDLs also attract phagocytes making the amount of drug actually delivered to the tumors and thence the therapeutic dose difficult to determine.

The use of solid matrix microspheres containing adsorbed drugs within the matrix is also known. For instance, U.S. Pat. No. 4,492,720 to Mosier disclosed methods for making microspheres to deliver chemotherapeutic drugs (including Cis-Platinum) to vascularized tumors. This method of preparing microspheres is accomplished by liquid encapsulation and solid-phase entrapment wherein the water-soluble drug is dispersed in a solid matrix material. The method involves dissolving the aqueous drug and the matrix material in a organic solvent, in which they are mutually soluble, then dispersing this mixture in a second organic solvent to form an emulsion that is stable enough for intravascular injection.

Other approaches have utilized copolymers such as polyvinyl chloride/acrylonitrile dissolved initially in organic solvents to form microparticles containing, for instance aqueous enzyme solutions. U.S. Pat. No. 3,639,306 to Sternberg et al. discloses a method of making anisotropic polymer particles having a sponge-like inner support structure comprising large and small void spaces and an outer, microporous polymer film barrier. A multiple-step batch process is used which entails removal of the organic solvents used to dissolve the polymers prior to addition of aqueous components. Solid-matrix microspheres, however, are often not perfect spheres thereby limiting the packing density. Additionally, many drugs cannot be trapped or adsorbed in these systems at effective concentrations and drug-release rates are often not constant.

Conventional methods of forming of multi-lamellar, immiscible, liquid microcapsules are limited, because of density-driven phase separation and stratification into horizontal layers resulting in the necessity to use multi-step, batch processing including mechanical mixing and solvent evaporation phases [Talsma and Crommelin 1992]. Each batch step suffers losses which reduce overall efficiencies. Conventional methods do not permit simultaneous formation of the outer skin as the microcapsule itself is formed. Many conventional therapeutic microspheres have natural phospholipid outer skins (usually in combination with cholesterol and a fatty amine) and therefore are subject to elimination by immune cells. Other conventional methods use sialic acid and other coatings on the lipid bilayer to mask the liposomes from detection by the scavenging systems of the body. Without an adequate outer skin, microcapsules often coalesce thereby reducing shelf-life.

For instance, U.S. Pat. No. 4,855,090 to Wallach, discloses a method of making a multilamellar lipid vesicle by blending an aqueous phase and a nonaqueous lipophilic phase using a high shear producing apparatus. The lipophilic phase is maintained at a high temperature (above the melting point of the lipid components) and is combined with an excess of the aqueous phase, which is also maintained at a high temperature. U.S. Pat. No. 5,032,457 to Wallach discloses a paucilamellar lipid vesicle and method of making paucilamellar lipid vesicles (PLV). The method comprises combining a nonaqueous lipophilic phase with an aqueous phase at high temperatures and high shear mixing conditions, wherein the PLVs are rapidly formed in a single step process.

U.S. Pat. No. 4,501,728 to Geho et al. discloses the encapsulation of one or more drugs or other substances within a liposome covered with a sialic acid residue for masking the surface of the membrane from scavenging cells of the body utilizing techniques known for the production of liposomes. In one embodiment, additional tissue specific constituents are added to the surface of the liposome which cause the liposome thusly treated to be attracted to specific tissues. Similarly, U.S. Pat. No. 5,013,556 to Woodle et al. provided methods for making liposomes with enhanced circulation times. Liposomes created by this method contain 1–20 mole% of an amphipathic lipid derivatized with a polyalkylether (such as phosphatidyl ethanolamine derivatized with polyethyleneglycol). U.S. Pat. No. 5,225,212 to Martin et al. discloses a liposome composition for extended release of a therapeutic compound into the bloodstream, the liposomes being composed of vesicle-forming lipids derivatized with a hydrophilic polymer, wherein the liposome composition is used for extending the period of release of a therapeutic compound such as a polypeptide, injected within the body. Formulations of "stealth" liposomes have been made with lipids that are less detectable by immune cells in an attempt to avoid phagocytosis [Allen et al. 1992]. Still other modifications of lipids (i.e., neutral glycolipids) may be affected in order to produce anti-viral formulations. U.S. Pat. No. 5,192,551 to Willoughby et al. 1993. However, new types of liposomes and microcapsules are needed to exploit the various unique applications of this type of drug delivery.

It is known that microgravity can be advantageously utilized to induce and maintain crystal growth due to the lack of density driven convective flow in liquids. U.S. Pat. No. 4,909,933 to Carter et al. discloses an apparatus for carrying out crystallization of proteins and chemical syntheses by liquid-liquid diffusion in microgravity environments. The apparatus comprises a housing having a plurality of chambers and a valve which separates at least two of the chambers so as to allow controlled fluid flow.

The disadvantages of conventional liposomes or microcapsules include manufacturing methods that require many batch process steps to: 1) form the liposomes, 2) remove unwanted organic solvents, detergents, and 3) harvest the proper size and shape microparticles for optimum pharmacologic efficacy [Talsma and Crommelin 1992]. Also conventional liposomes often use natural lipids and lectins (from eggs, soybeans and other inexpensive sources) which attract phagocytic immune cells that rapidly remove the liposomes from the circulatory system before they arrive at the target tissue. This creates variable dose-responses making calculations of pharmacokinetics and therapeutic doses very difficult [Allen 1988]. Major difficulties with commercial preparation of microcapsules often involves density-driven phase separation of the immiscible carrier fluids, esp. when forming water/oil systems.

These drawbacks limit the yield, make it difficult to harvest the proper size particle, and often result in microparticles that are not spherical nor uniform in size, thereby limiting the packing density (and drug payload delivered) when the microcapsules arrive at the arterioles or capillaries in the target issues. Liposomes have a bilayer outer membrane which requires that the entrapped drug must be soluble in both the aqueous and lipid phases in order to outwardly diffuse. This limits the type of drugs that can be released from conventional liposomes and the mole ratio of aqueous to lipid phases limits the amount of drug which can be delivered.

Processes are needed for forming spherical multi-lamellar microcapsules having alternating hydrophilic and hydrophobic liquid layers, surrounded by flexible, semi-permeable hydrophobic or hydrophilic outer membranes which can be tailored specifically to control the diffusion rate. In particular, methods of making such microcapsules are needed which do not rely on batch processes involving density-driven phase separation and stratification into horizontal layers, mechanical mixing and solvent evaporation phases. Moreover, there is clearly a need for methods and compositions which allow for uniform size and more spherical microcapsules. Such improved microcapsules would be particularly useful in the delivery of pharmaceutical compositions.

SUMMARY OF THE INVENTION

Processes and compositions are provided by the present invention which overcome certain of the limitations of prior methodology for forming microcapsules. In particular, methods and compositions are provided which form multi-lamellar microcapsules having alternating hydrophilic and hydrophobic liquid layers, surrounded by flexible, semi-permeable hydrophobic, outer membranes which can be tailored specifically to control the diffusion rate. In particular, the methods of making microcapsules provided by the present invention do not rely on batch processes such as density-driven phase separation and stratification into horizontal layers, mechanical mixing or solvent evaporation. Encapsulation of cytotoxic or labile drugs in such microcapsules enables targeted delivery and sustained release kinetics that are not currently available with intravenous injection.

The invention provides, in one aspect, methods of making a multi-layered microcapsule. The term microsphere as used herein is a general term which can include any spherical microscopic vesicle including microspheres, micelles, inverted micelles, bilayer vesicles and liposomes. The term microcapsule as used herein is a more specific term which refers to a microsphere which comprises at least two layers, one of which is innermost and is substantially completely enclosed within the other. In a distinct break from traditional methods for making microcapsules, the methods of the invention rely on low shear mixing and liquid-liquid diffusion process, particularly as developed for forming microcapsules that may contain both aqueous and hydrocarbon soluble drugs.

The terms multi-layered and multi-lamellar are used interchangeably throughout the specification and claims and both refer to the fact that the microcapsules of the invention comprise at least two immiscible layers nested around one another. In some instances, the core layer will be hydrophobic in nature and will be completely surrounded by at least one neighboring hydrophilic layer. In others, the core layer will be hydrophilic in nature and will be completely surrounded by at least one neighboring hydrophobic layer.

The basic method of the invention relies on liquid-liquid interactions. In the basic method, the first step entails formulating a first phase or layer while the second step entails formulating a second phase or layer. The two phases or layers are formulated to be immiscible with one another. For the purposes of this invention, "immiscible" means that the solubility of one phase or layer is not more than 10 gm/100 ml in an adjoining phase or layer and that the two adjoining phases or layers form an interface resembling a meniscus.

Formulating the first phases or layer comprises combining a first solvent, a first polymer or microcapsule layer-forming compound soluble in the first phase, a co-solvent, an oil, and water. The first solvent will typically comprise about 75–90% by volume of the first phase. The first polymer is selected to be one soluble in the first phase and typically will comprise about 1–5% by volume of the first phase. A small amount of a co-solvent is also added to the first phase, which co-solvent may also function as a co-surfactant. Oil comprising about 1–10% by volume is also added to the formulation. The first phase will also contain about 1–5% water by volume.

The method next calls for formulating a second phase immiscible with the first phase. The second phase comprises a second solvent, a second polymer soluble in the second phase, a surface active agent, and a salt. The relative, approximate volume percentages of these constituents is about 70–98% second solvent, 1–10% second polymer, 1–4% surface active agent, and 1–3% salt.

In order to ensure that the liquid-liquid interactions necessary to form the microcapsule will occur, certain of the constituents of each phase are selected relative to one another. Thus, the surface active agent in the second phase is selected such that it will have a hydrophilic/lipophilic balance value greater than that of the first polymer constituent of the first phase. Generally, the most useful surface active agents have been found to be those which are non-ionic and which have a hydrophilic/lipophilic balance value of 10.0 or greater. Next, the second polymer constituent of the second phase is selected to have a hydrophilic/lipophilic balance value lower than that of the surface active agent constituent of the same phase. While not an exhaustive list, certain hydrophilic/lipophilic balance values of materials which may be used in the formulations of the invention are provided below.

| HYDROPHILIC/LIPOPHILIC BALANCE (HLB) (McCutcheon 1979) | |
|---|---|
| Compound | HLB |
| Glycerol trioleate | 0.8 |
| Cholesterol | 1.0 |
| Triglyceride of coconut oil | 1.4 |
| Sorbitan trioleate | 1.8 |
| Sorbitan tristearate | 2.1 |
| Glycerol monooleate | 2.7 |
| Mono and di glycerides of fat burning fatty acids | 2.8 |
| Glycerol Monostearate (GMS) | 2.8–5.0 (3.8 preferred) |
| Propoxylated ethylene diamine plus ethylene oxide | 3–28 |
| Mono/diglyceride | 3.2 |
| Glycerol mono coconut | 3.4 |
| Mono/diglyceride | 3.5 |
| Propylene glycol mono fatty acid ester | 3.5 |
| Monoethoxyl lauryl ether | 3.6 |
| Stearyl lactyl acid | 3.8 |
| Hydrogenated cottonseed oil | 3.8 |
| Mono and diglycerides with citric acid or lactylated ester or fatty acid | 4.2–4.6 |
| Ethoxylated fatty amine (2 moles ETO) | 4.5 |
| Diethylene glycol monostearate | 4.7 |
| Sorbitan monopalmitate | 4.7 |
| Diethylene glycol monostearate and oleate | 4.7 |
| Ethoxylated (2) cetyl ether | 5.3 |
| Glycerol Monoricinoleate | 6.4 |
| Glycerol monolaurate | 6.8 |
| Triglycerol mono stearate | 7.0 |
| Polyethylene glycol (400 dioleate) | 7.2 |
| Lanolin sterol | 8.0 |
| Ethoxylated nonyl phenol (CO-420 & CO 850) | 8.0–16.0 |
| Polyethylene glycol (400) distearate | 8.2 |
| Sorbitan monolaurate | 8.6 |
| Ethoxylated sorbitan fatty acid esters and alkyl/aryl alcohol | 9.0 |
| Anhydrous lanolin | 10.0 |
| Polyethylene glycol monostearate | 11.0 |
| Polyethylene glycol 400 | 11.2 |
| Ethoxylated (10) cetyl ether | 12.9 |
| Ethoxylated glycerol monostearate (gms) | 13.1 |
| Sorbitan monostearate | 14.9 |
| Sorbitan monooleate with 20 moles ethylene oxide | 15.0 |
| Ethoxylated (20) oleyl ether | 15.3 |
| Ethoxylated (20) stearyl cetyl ether | 15.8 |
| Ethoxylated castor oil | 18.0 |
| Nonyl phenol polyethylene glycol ether | 18.1 |
| Polyethylene glycol 600 mono laurate | 19.6 |
| Sodium lauryl sulfate | 40 |
| Propylene glycol monostearate | 40 |
| Hydroxylated lanolin sodium oleyl sulfate | 42 |
| Blends of GMS and sorbitan monooleate with 20 mols ethylene oxide | 52 |

The basic method next involves creating an interface between the first and second phases. The creation of the interface is achieved in such a way that minimal shear and mixing occurs between the phases. The two immiscible phases are brought together in such a mechanical manner that the fluid shear properties are controlled to low levels, below about 12 dynes/cm$^2$, and such that the adsorptive surface properties at the immiscible interfaces are not significantly altered. Although the exact mechanisms are not fully understood, the inventors believe that the maintenance of certain surface properties, such as the surface tension, Helmholtz charge distribution (electrical double layer), and partitioning of the surfactant molecules between the immiscible phases must remain substantially intact so that lateral phase separation can occur in a manner which allows simultaneous formation of multiple liquid interfaces (oil/water or water/oil) and which results in microcapsules having alternating spherical shells of hydrophilic and hydrophobic liquid layers. This is believed to be the mechanism for the formation of multi-lamellar vesicles which are formed in a single step. Although this can best be demonstrated under microgravity conditions, wherein buoyant convection is absent and diffusion-driven convection predominates, this also can be accomplished in unit gravity conditions by balancing the density differences between the two liquid phases or by any other mechanical means which prevents excess fluid shear from significantly altering the normal adsorptive surface properties which are determined by the chemical composition of the formulas and the interfacial phenomena among the solvents, polymers and surfactants. In a preferred embodiment, the creation of the interface will occur by sliding individually separated compartments containing the two phases into register with one another in a manner that substantially limits shear and provides gentle mixing.

In the final step of the basic method, conditions are established in order to substantially limit all mixing between the interfaced liquid phases. In the most preferred environment, the two phases would be allowed to interact at their interface without agitation, stirring, shearing or like force. It is preferred to also limit even those quiescent forces such a gravity-controlled sedimenting, shifting, drift and the like. Thus, in certain preferred embodiments, only chiefly diffusion-driven convection is used to spontaneously form microcapsules, as the chemical formulations of the different phases assist in lowering the surface free energy across the interface. It is also at this time that formation of the polymeric outer coating is initiated.

In one embodiment, the two liquids thus formulated are separated into distinct compartments or spaces which spaces are each connected to a central diffusion chamber into which each compartment can deliver its resident liquid loading. The compartments are initially closed to access into the central diffusion chamber so that the first and second liquids are kept apart from one another and not allowed to interact. While it is possible to use any number of devices to achieve this separation, a preferred device is a device like the Materials Dispersion Apparatus described in more detail below. The separation of the two liquids is maintained until both liquids and the device containing them can be placed in an environment in which convective mixing may be minimized, such as in a microgravity environment.

The methods of the invention are slightly different depending upon whether the first solvent is selected to be organic or aqueous. Where an organic solvent is used to formulate the first phase, that organic solvent is selected from the group of organic solvents consisting of ethyl alcohol, methyl alcohol and isopropyl alcohol. Where an organic first solvent is used to formulate the first phase, the first polymer is selected to be one soluble in the organic solvent selected. Such a first polymer may be selected from the group of polymers consisting of glycerol monosterate, glycerol monooleate, glycerol monolaurate, glycerol dioleate, glycerol disterate, cholesterol, stigmasterol, phytosterol, campesterol, and lecithins such as phosphatidyl cholines (e.g., Centrolex-F™).

Where the first solvent is aqueous, a slightly different approach is taken. In those instances, the first polymer is again requisitely soluble in the first aqueous phase and may be selected from the group of polymers consisting of polyvinyl pyrrolidone, polyvinyl alcohols, gelatin, gum tragacanth, carrageenan, Karaya gum, Guar gum, gum arabic, alginates, carboxymethyl cellulose, hydroxypropyl cellulose, carboxypropyl cellulose, and lecithins.

Regardless of the formulation with an aqueous or organic first solvent and polymer, the methods of the invention both use a co-solvent which may be selected from the group of co-solvents consisting of $C_3$–$C_8$ alcohols, tetrahydrofuran, dioxane, acetonitrile, dimethylformamide, dimethylacetamide, and dimethyl sulfoxide. Similarly regardless of the organic/aqueous nature of the first solvent and polymer used, the methods of the invention add to the formulation of the first phase an oil. These oils may be selected from the group of oils consisting of unsaturated oils such as poppy seed oil, olive oil, peanut oil, sesame oil, cotton seed oil, soybean oil, safflower oil, corn oil, sunflower seed oil and canola oil or saturated oils such as mineral oil, long chain paraffinic oil, and liquid petrolatum. In a preferred embodiment, poppy seed oil will be iodinated to form iodinated poppy seed oil (IPO) and incorporated into a microcapsule as a marker or tracer for tracking the presence of the microcapsule once injected via radiocontrast detection methods known well to those of skill in the art of radiography.

Whether the method involves an organic or an aqueous first solvent, the second polymer, the surface active agent and the salt may each be selected from a particular group of such compounds. The second polymer may be selected from the group of polymers consisting of polyethyleneglycol 1000–8000 daltons, dextran 1000–10000 daltons, polyvinylpyrrolidone, polyvinyl alcohols, gelatin, gum tragacanth, carrageenan, Karaya gum, Guar gum, gum arabic, alginates, carboxymethyl cellulose, hydroxypropyl cellulose, carboxypropyl cellulose, and lecithins. The surface active agent is selected from the group of surface active agents consisting of sorbitan monooleate treated with ethylene oxide, dextran, polyethylene glycol, $C_{12}$–$C_{20}$ fatty acids, 2-amino-2-methyl-1-propyl aminomethyl propanol amphoteric salts and quaternary ammonium salts. The salt is selected from the group of salts consisting of NaCl, KCl, $CaCl_2$, $MgCl_2$, quaternary ammonium salts, cetyl trimethylammonium bromide and 4-methoxy-4(3-phosphatidyl choline)spiro(1,2-dioxetane-3-g,l-adamantane) disodium salt.

In certain embodiments of the methods of the invention, pharmaceutical compositions will be incorporated into the microcapsule. Where such pharmaceuticals are thusly incorporated, they may be introduced initially as a solute or as particulates suspended in one or the other of the liquids used to formulate the layers of the microcapsules. In certain embodiments, the pharmaceutical is introduced in one of the phases or layers used to produce the microcapsule at a concentration sufficient to allow nascent crystal formation within said microcapsule. Crystal formation may occur at or near the time of formation of the microcapsule containing the dissolved pharmaceutical material. The aqueous solvent system used to dissolve an aqueous-soluble pharmaceutical is selected to permit water molecules to migrate away from the drug-containing layer into the alcoholic mixture. The process of crystal formation is likely to be promoted in this manner after formation of the microcapsule. In fact, it is possible to enhance the crystallization process after the microcapsule is formed by controlled transport of the solvent phase or layer in which the pharmaceutical to be crystallized is a solute. It certain embodiments, the crystal thus formed may take up most of the internal capacity of the microcapsule.

Multi-layered microcapsules, with both hydrophobic and hydrophilic drug compartments, as produced by the methods of the invention enable diffusion of complimentary drugs from the same microcapsule, e.g. antibiotics and immunostimulants to treat resistant infections or multiple fibrinolytic drugs to dissolve emboli. Co-encapsulation of radio-contrast medium as provided herein enables oncologists to monitor the delivery of anti-tumor microcapsules to target tumors using computerized tomography and radiography that track the distribution of microcapsules after release from the intra-arterial catheter. Such microcapsules will have important applications in chemotherapy of certain liver, kidney, brain and other tumors.

The diameters of microcapsules possible to attain using the methods of the invention are also of particular usefulness in medical applications. Thus, whereas prior art methods have been able to routinely produce microspheres over 1–10 micron average sizes, the present invention's methods provide similarly-sized microcapsules of 1–20 micron diameters for intravenous administration. Also provided are 50–300 micron sized microcapsules particularly useful in interarterial chemoembolization of tumors, and microcapsules in the range of 300 micron and greater diameters useful in interperitoneal administered drugs.

The pharmaceutical composition encapsulated in the microcapsule may be one soluble in aqueous solutions or may be one soluble in organic solutions. This, of course, governs the selection of the phase or layer in which the pharmaceutical composition is formulated. The microcapsules of the invention and methods for producing them are of particular utility when formulating organic-soluble drugs as these type of drugs are otherwise very difficult to administer. The pharmaceuticals may be those selected from the group of such widely diversified pharmaceutical compositions as that consisting of cytoxins, proteases, cytokines, anti-nauseants, steroids, anti-fungal agents, fibrinolytic enzymes, and antibiotics. The inventors have successfully encapsulated representatives of these classes of pharmaceuticals using the methods of the invention. It is also possible to incorporate a pharmaceutical composition which is not initially dissolved in one or another of the phases or layers, but rather which drug is in suspension. As noted above, depending upon its solubility and upon where the pharmaceutical chemist wishes to locate the drug, it is possible to formulate a drug in any of the phases or layers, by dissolving or suspending the drug as needed.

The methods of the invention surprisingly demonstrated the ability to package very high concentrations of drugs in the layers formed. It is possible, using the methods of the invention, to formulate a pharmaceutical at a concentration sufficient to allow nascent crystal formation within the microcapsule once it is formed. These microcapsules, due in one regard to their being constructed with outer polymeric coatings, are also particularly flexible yet rugged (able to withstand shear forces greater than 10 dynes/cm$^2$). As will be related specifically below, microgravity experiments, on sounding rockets (1989–92) and Shuttle missions STS-52 (1992) and STS-56 (1993) using an automated Materials Dispersion Apparatus, produced multi-lamellar microcapsules containing both Cis-platinum (anti-tumor drug) and iodinated poppy seed oil (a non-radioactive, radiocontrast medium), surrounded by a polymeric skin. Microcapsules formed with amoxicillin (antibiotic) or urokinase (a clot dissolving enzyme), co-encapsulated with IPO, were still intact after two years after return to 1×g environments. In many instances, microcapsules were formed with the Cis-Platinum or amoxicillin so concentrated that crystals of the drugs formed inside.

Surprisingly, the methods of the invention have demonstrated a unique ability to encapsulate such saturated drug solutions, and since the overall partitioning characteristics between immiscible layers facilitates solvent transport out of the aqueous layer, it is possible to concentrate the drug to the point that formation of drug crystals occurs within the microcapsules. This ability of the microcapsules and methods of the invention provides the maximum drug payload per microcapsule and the best drug release kinetics for prolonged treatment at maximum drug diffusion rates.

Microcapsules containing a large volume component of crystalline drug provide the most concentrated drug possible when it is released at the target site. Until the crystals are completely dissolved, the drug release rate is independent of time (zero order release kinetics). When the crystals have dissolved, the drug release rates revert to first order kinetics (exponential with time). The encapsulated crystals of the invention are in the range of 1–50 microns in diameter. Since these crystals are precipitated in situ, they are quite different from the other commercially-available crystalline drug delivery systems (e.g., Microcrystal™) which use phospholipids to encapsulate tiny particles or crystals of drugs with an average diameter of only 0.3–1.0 micron [Parikl and Stern 1994].

It is also possible to additionally treat the microcapsules thus formed with additional steps. In some instances, the methods of the invention, regardless of whether they initially use an organic or an aqueous first solvent, formulate a third phase comprising an oil or $C_{20}$–$C_{38}$ paraffin and, contact the formed microcapsule with the third phase. In other instances, the methods of the invention form a two-layered microcapsule, then formulate a third phase comprising an aqueous solution and, contact the formed microcapsule with the third phase. The basic method and alternatives are summarized below.

|  | Group 1 | Group 2 |
| --- | --- | --- |
| Solution 1 | Solvent 1 is a hydrocarbon | Solvent 1 is aqueous |
|  | Polymers are hydrocarbon soluble, selected to form the outer coating (typically of lower HLB values) | Polymers (skin) are water soluble, but can be extended into organic phase (includes phospholipids) Ex. Centrolex F ™ |
|  | Co-solvents alcohols, hydrocarbons (act as co-surfactants) | Co-solvents same, but often less % |
|  | Oils saturated or unsaturated oils | Oils same |
|  | Drug dissolved (or suspended particulate) | Drug dissolved (or particulate) |
| Solution 2 | Solvent 2 aqueous | Solvent 2 same |
|  | Polymers water soluble (PEG, Dextran) | Polymers same |
|  | Surfactants (typically higher HLB value) | Surfactants same but often less % |
|  | Salts ionic, quaternary ammonium salts | Salts same, but often different % |
|  | Drugs aqueous soluble | Drugs aqueous soluble |
| Solution 3 | Oils hydrocarbons | Oils same |
|  | Polymers hydrocarbon-soluble | Polymers same |
|  | Drugs can be included | Drugs can be included |
|  | -- OR -- | -- OR -- |
|  | Alternative aqueous solution coating-adjuvants immuno-globulins | Alternative aqueous solution coating same |
|  | polymers - aqueous soluble surfactants - | polymer same surfactants same |

Traditional emulsion methods form a O/W/O (oil/water/oil) or W/O/W (water/oil/water) liquid system which is designed to retain the internal phase(s) within the external solvent unless the emulsion is broken, whereupon the liquid phases separate. In the methods of the invention, the use of surfactants and co-surfactants permits formation of an emulsion of large spheroids (not small microspheroids) of one phase dispersed in the other phase configured in a sphere. The sphere is also surrounded by another immiscible liquid layer (opposite phase to that of the innermost liquid sphere) and then (often) this multi-layered sphere is contained in another opposite-phase liquid layer and finally the entire multi-layered sphere is contained in an outer skin. The results of the process of the invention are not to form a traditional O/W/O or W/O/W emulsion (which is a fine dispersion of one phase in another), but rather to form multi-lamellar, alternating immiscible-layer microcapsules contained within a thin, semi-permeable outer skin. In the microcapsules of the invention, the immiscible phases are distinct and separated according to the surface tension characteristics of the liquids at each interface, hence there is no true emulsion maintained by the surfactant which could be broken.

Thus, in certain embodiments of the methods and compositions of the invention, the multi-layered microcapsule will be produced which comprises at least three alternating layers or phases. Thus, if the first layer is an aqueous layer or core, the next layer may be an organic layer. This organic layer may then be covered over by a second aqueous layer which forms on its outer surface a polymeric skin. Conversely, the liquid at the core of the microcapsule may be an organic liquid layered over by an aqueous layer followed by another organic layer which forms a polymeric skin over the surface of the microcapsule. Certainly, extension of these basic formulations may be envisioned where four or more layers are possible or where multiple skins or coatings are utilized.

Whether used in conjunction with a two-layer microcapsule or with microcapsules with more than two layers, the coatings of the present invention are of substantial utility, particularly when the methods are carried out at earth-normal gravity. The coatings can be either substantially of a hydrophobic nature or of a hydrophilic nature as described below and are derived from addition of certain polymers in the initial formulations of the liquids used to make the microcapsules. Where hydrophobic coatings are used in conjunction with drug-delivery systems, the coatings are selected for their complementary permeability to the drug to be delivered. The polymers are also selected for their flexible characteristics after formation and curing which is of particular utility during intravascular transport and allows higher packing densities for forming emboli such as in chemoembolization therapy. Thus, for example where a water-soluble drug is to be delivered, the drug is contained in an inner aqueous layer over which is placed a coating permeable to the dissolved drug. Preferably, the coating material should be impermeable to solvents or oils. The coatings which have been observed to be deposited on the surfaces of the microcapsules of the invention are about 0.01–2.0 microns thick where the coating is a hydrophobic coating, and about 0.1–5.0 microns thick where hydrophilic coatings are deposited.

The additional steps and third formulated phases may also be used advantageously to provide the microcapsule with specific characteristics. Thus, the third phase may further comprise a pharmaceutical composition which is added to the formed surface of the microcapsule. The third phase may also be used to add a pharmaceutical composition such as an adjuvant. The adjuvant may further comprise an immunoglobulin, other protein, hydrocolloid or polysaccharide. This is of particular utility in designing microcapsules with unique immunologic, pertinacious or other surface characteristics which makes them selectively adhere to certain target tissues (cells) or renders the microcapsules attractive to certain phagocytic cells (when the cells are the actual target for the therapeutic drug). Where the adjuvant is a hydrocolloid, it may be selected from the group of such hydrocolloids consisting of collagen, isoelectric gelatin, agar, gum arabic, gum tragacanth, alginates, cellulose derivatives and carrageenans. The third phase may also further comprise a surface active agent.

The third aqueous phase can also contain a chemical activator which acts upon the inactive form of the pharmaceutical agent (drug) as it diffuses out of the inner layers of the microcapsule. The function of the activator is to chemically convert the inactive drug to its active form just before it is released from the microcapsule. This is illustrated when the pharmaceutical is a pro-enzyme and where the activator is another proteolytic enzyme which cleaves the pro-enzyme at active site to render the molecule biologically active. This embodiment can be used to deliver very labile drugs which have very limited shelf-lives or short biological half-lives whereupon the activator (third phase) can be added shortly prior to intravascular administration such that the inactive drug becomes activated after the microcapsules have reached the target site. This can maximize the therapeutic effectiveness of the short-lived drug at the target site of action.

One or more of the phases of the microcapsule of the invention may further comprise fluorescent molecules selected from the group of fluorescent molecules consisting of fluoresceins, cyanins, naturally fluorescent molecules, and rhodamines. This is particularly useful where radiocontrast media are not desirable or where an additional tracking method is useful or where it is of value to monitor the presence or absence of a layer in the microcapsule, fluorescent molecules may be incorporated into the microcapsule of the invention. Thus, for instance, as described more fully below, it may be useful to incorporate a hydrophilic fluorescent molecule in the aqueous liquid in order to determine the relative location and number of aqueous liquid layers in a certain production batch of microcapsules produced by the methods of the invention.

Critical to the success of the methods of the invention is the substantial limitation of mixing between said phases to diffusion-driven convection. One manner in which to so limit other types of mixing is to carry out the methods under microgravity. Microgravity is defined as a gravity force of less than $1 \times 10^{-3} \times g$. Such gravitational environments may be achieved in a variety of ways, at least some of which are detailed herein. For instance, microgravity may be achieved in certain trajectories of sounding rockets. Even longer periods of microgravity may be obtained with temporary orbiters such as the space shuttle. Relatively indefinite periods of microgravity may be obtained in permanent or semipermanent orbital space craft such as the orbital space station and other geosynchronous orbital satellites. The exposure of the first and second liquids to microgravity has been found to be effective in forming the microcapsules of the invention where the exposure is at least 6.5 minutes in duration. Certainly, as described more fully below, greater exposure periods have also been proven successful. The inventors anticipate that periods of exposure as short as 1.0 minute will also produce adequate numbers of microcapsules.

In preferred embodiments, however, the methods of the invention will not use microgravity in order to limit mixing between the phases. Of course, such limitations of mixing can be promoted by carrying out the methods below ambient temperature. Limitation of interactions between the phases is best promoted by substantially balancing the specific gravity between said phases as is described below. The formulations and methods necessary to achieve earth-normal microcapsule formation are described in greater detail herein. In either case, or in combinations of these techniques, mixing between the two phases may be chiefly the result of diffusion-driven convection.

The inventors have found that there is a greater size distribution which results from microencapsulation at earth-normal gravity. At least a partial reason for this wider size distribution is apparently the inability under earth-normal gravity to avoid certain sedimentation phenomena alone and sedimentation effects combined with weight-related contact of sedimented microcapsules. These facts require some additional manipulation under earth-normal environments not required in the 0×g environments—namely, sieving of the resulting microcapsules in order to generate more uniform fractions. Therefore, at earth normal gravity, the utility of the outer coating of the microcapsules of the present invention become even more important. Enhancing the ruggedness of the earth-normal microcapsules by curing and other steps as related herein may also be used.

A preferred method of making a multi-layered microcapsule comprises: formulating a first phase comprising an organic solvent selected from the group of organic solvents consisting of ethyl alcohol, methyl alcohol and isopropyl alcohol, a first polymer soluble in the first phase selected from the group of polymers consisting of glycerol monosterate, glycerol monooleate, glycerol monolaurate, glycerol dioleate, glycerol disterate, cholesterol, stigmasterol, phytosterol, campesterol, lecithins such as phosphatidyl cholines (e.g., Centrolex-F™), a co-solvent selected from the group of co-solvents consisting of $C_3$–$C_8$ alcohols, tetrahydrofuran, dioxane, acetonitrile, dimethylformamide, dimethylacetamide, and dimethyl sulfoxide, an oil selected from the group of oils consisting of poppy seed oil, olive oil, peanut oil, sesame oil, cotton seed oil, soybean oil, safflower oil, corn oil, sunflower seed oil, canola oil (unsaturated oils), or mineral oil, long chain paraffinic oil, and liquid petrolatum (saturated oils), and water; formulating a second phase immiscible with the first phase, the second phase comprising water, a second polymer soluble in the second phase selected from the group of polymers consisting of polyethyleneglycol 1000–8000 daltons, dextran 1000–10000 daltons, polyvinylpyrrolidone, polyvinyl alcohols, gelatin, gum tragacanth, carrageenan, Karaya gum, Guar gum, gum arabic, alginates, carboxymethyl cellulose, hydroxypropyl cellulose, carboxypropyl cellulose, lecithins, a surface active agent selected from the group consisting of sorbitan monooleate treated with ethylene oxide, dextran, polyethylene glycol, $C_{12}$–$C_{20}$ fatty acids, quaternary ammonium salts, and a salt selected from the group of salts consisting of NaCl, KCl, $CaCl_2$, $MgCl_2$, quaternary ammonium salts, cetyl trimethylammonium bromide, 2-amino-2-methyl-1-propyl aminomethyl propanol, and 4-methoxy-4(3-phosphatidyl choline)spiro(1, 2-dioxetane-3-g,1-adamantane) disodium salt; the surface active agent having a hydrophilic/lipophilic balance value greater than that of the first polymer; the second polymer having a hydrophilic/lipophilic balance value lower than that of the surface active agent; creating an interface between the first and second phases in a manner that substantially limits fluid shear; and, substantially maintaining adsorptive surface characteristics of said interface.

Microcapsule products produced by any of the methods of the invention are also claimed. The methods of the invention are used to form unique multi-lamellar, microcapsules, having alternating hydrophilic and hydrophobic liquid layers surrounded by a flexible, semi-permeable, polymeric outer "skin". The outer skin which can be either hydrophilic or hydrophobic, is designed to allow controlled drug diffusion out of the microcapsule.

Unlike any natural phospholipid or other component of cell membranes, the outer skin of the microcapsules of the invention avoids recognition and phagocytosis by immune cells, thereby increasing the amount of drug delivered to the tissues. The multi-layered microcapsules of the invention can entrap multiple drugs in different solvent compartments and saturated solutions of drugs which may then form crystals inside the microcapsule. Radiocontrast medium can be co-encapsulated with drugs in the same microcapsule. A magnetic resonance contrast agent can also be encapsulated such as various metallo-organic compounds including aqueous soluble ferrous gluconate, Gadolinium diethylene triamine pentaacetic acid and hydrocarbon-soluble, iron pentacarbonyl.

The microcapsules of the invention have been found to provide a surprisingly uniform distribution of diameters (FIG. 3A and B). This uniformity is particularly important in its medical applications. The microcapsules thus produced can be used to deliver several drugs which can be released sequentially to the target tissues. The deformable, liquid-filled microcapsules also have advantages over solid matrix microspheres in achieving maximum packing density in blood vessels, thereby decreasing blood flow to target tissues. This enhances the therapeutic effect of combined drug delivery and reducing the blood supply to vascular tumors (chemoembolization).

The methods of the invention result in more spherical, uniform size distributions of microcapsules. When comparing certain prior art equipment and methods for forming microcapsules (Microfluidics, Inc., see FIGS. 2A, B and 3A, B), the inventors found that even the preferred formulations of the invention were incapable of providing such uniformity. In certain instances, hardly any microcapsules formed at all where mixing and vortexing were used to distribute one phase into the next (FIG. 2A). In others, poorly formed and non-spherical microcapsules resulted (FIG. 2B). In contrast to the failures of the prior art methods, the methods of the invention were successfully used to generate uniform, spherical microcapsules both under unit gravity (FIG. 3A) and under microgravity conditions (FIG. 3B). Such uniformity enables superior drug delivery. Enhanced uniformity also enables better dose distribution calculations for establishing the therapeutic dose in the treatment of specific diseases, especially treatment of certain types of tumors. Importantly, the methods of the invention allow the formation of larger-sized, multi-lamellar microcapsules (1–350 micron) than heretofore possible. Such a capability allows multilamellar microcapsules to be made specifically for inhalation and deposition in the lungs. This uniformity allows facile sieving or filtering of the microcapsule products in order to obtain highly uniform diameter fractions.

Most liposomes have a very small hydrophobic compartment and therefore can only carry small amounts of hydrophobic drugs. Contrastingly, the microcapsules of the invention have a relatively large hydrophobic liquid compartment which enables delivery of more hydrophobic drug per microcapsule. Moreover, the microcapsules of the invention have relatively large hydrophilic and hydrophobic compartments which permits tandem delivery of both water soluble and non-water soluble drugs in the same microcapsule.

As previously noted, the microcapsules of the invention may contain polysaccharides. Inclusion of such polysaccharides is one of several aspects of the methods of the invention that enhance the formation of the microcapsules. The inclusion of injectable polysaccharides in the formulations of the invention (similar to those polysaccharides found in Ringer's solutions) contributes to the driving forces that control phase separation and phase partitioning of the entrapped drugs. The polysaccharides also provide increased shelf-life and stability of the parenteral suspensions. Use of the osmotically neutral salt solutions in the aqueous phase enhances micelle formation, lateral phase separation, and increases the dispersion of microcapsules and their stability as they are formed.

The methods of the invention in a preferred embodiment utilize a non-phospholipid outer coating. The microcapsules formed by this method are contained in a thin, semipermeable, outer membrane comprised of hydrophobic (e.g. mono- or polyglycerides or waxy-polymers) or hydrophilic polymers (e.g., PVA or PVP), depending on the desired diffusion release rate of the encapsulated drug. Thus, the coating has the advantage of allowing design of the appropriate drug diffusion and release characteristics while avoiding certain of the disadvantages of conventional liposomes (and lipid bilayers). In particular, the coating produced by the methods of the invention around the outer surface of the microcapsule avoids being readily detected and largely eliminated by the reticuloendothelial system (RES). The outer skin protects the microcapsules against shear forces encountered during manufacturing processes and during transport within the vascular system enroute to the target tissues. The hydrophobic outer membrane also can be designed to retard oxygen transport, thereby reducing oxidative degradation of the entrapped drug and improving the shelf-life of the parenteral suspensions. The flexible/deformable outer skin on the microcapsules of the invention results in increased packing densities within vascular beds. This results in microcapsules superior to solid microspheres (e.g. gelatin, albumin or starch) commonly used for chemoembolization therapy against tumors. The formulations used to produce the microcapsules of the invention are summarized below.

| | Formulas for Primary, Secondary and Tertiary Solutions for Microencapsulation | | |
|---|---|---|---|
| | Primary Solution (also can contain drug) | Secondary Solution | Tertiary Solution (also can contain dissolved drug) |
| Group 1 | First Solvent | Second Solvent | Oils (up to 100%) |
| | (75–90%) | water (70–98%) | IPO |
| | ethyl alcohol methyl alcohol | Polymers (1–10%) | heavy mineral oil olive oil |
| | isopropyl alcohol Organic Co-solvent 0–20% | polyethylene glycol PEG - 1000–8000 (polysaccharides) | same as in primary soln. paraffins ($C_{20}$–$C_{38}$) |
| | $C_4$–$C_8$ alcohols | Dextran 4000– | Alternative |
| | tetrahydrofuran (THF) dioxane acetonitrile | 20000 (range 10000– 100000)) | Aqueous solutions containing - immunoglobulins albumin |
| | dimethylformamide (DMF) dimethyl sulfoxide (DMSO) | polyvinyl-pyrrolidone polyvinyl alcohols Surfactants (ionic | gelatin hydrocolloids plant sterols phospholipids |

| | Formulas for Primary, Secondary and Tertiary Solutions for Microencapsulation -continued | | |
|---|---|---|---|
| | Primary Solution (also can contain drug) | Secondary Solution | Tertiary Solution (also can contain dissolved drug) |
| | Polymers (1–5%) (mono-glycerated) | and non-ionic) (1–4%) sorbitan | polysaccharides starches cyclodextrins |
| | glycerol monostearate glycerol monooleate glycerol monolaurate (polyglycerides) | monooleate plus ethylene oxides Dextran PEG $C_{12}$–$C_{20}$ fatty acid quaternary $NH_4$ salt | Polymers Surfactants (1–4%) (ionic and non-ionic) long chain amphoteric salts |
| | glycerol dioleate glycerol distearate (sterols) | Additional Polymers (1–10%) (hydrocolloids) | celluloses Additional Polymers Same as secondary |
| | cholesterol plant sterols - stigmasterol phytosterol campesterol (phospholipids) | gelatin gum tragacanth carrageenans karaya gum guar gum alginates | solution Dissolved Drugs (1% to saturation) soluble therapeutic |
| | lecithins | (celluloses) | |
| | e.g., phosphatydl choline (Centrolex-F ™) | celluloses (CMC, WEC, HPC) Salts (1–3%) | |
| | Water (1–5%) Oils (unsaturated or saturated) (1–10%) | water NaCl KCl, $CaCl_2$, quaternary $NH_4$ salts, cetyl | |
| | iodinated poppy seed oil (IPO) mineral oil cotton seed oil olive oil safflower oil canola oil peanut oil sesame oil corn oil Dissolved Drugs (1% to saturation) | trimethylammonium bromide, 2M2A-AMP, PPD Dissolved Drugs (1% to saturation) therapeutic of choice | |
| Group 2 | Aqueous First Solvent water (70–90%) | Same as Group 1 Co-Solvents Same as primary solution | Oils (up to 100%) Same as Group 1 Alternatives |
| | Co-solvents (0–20%) | Polymers (1–10%) | Aqueous solutions Same as Group 1 |
| | $C_3$–$C_8$ alcohols tetrahydrofuran (THF) dioxane acetonitrile dimethylformamide (DMF) dimethyl sulfoxide (DMSO) Polymers hydrophilic (water soluble) | Same as Group 1 Surfactants (1–20%) (ionic and non-ionic) Same as Group 1 Additional Polymers 1–10% Salts (1–3%) Same as Group 1 Dissolved Drugs 1% to saturation | Surfactants Same as Secondary Solution Dissolved Drugs 1% to saturation |
| | polyvinyl-pyrrolidone (PVP) polyvinyl alcohols (PVA) | | |

-continued

Formulas for Primary, Secondary and Tertiary Solutions
for Microencapsulation

| Primary Solution (also can contain drug) | Secondary Solution | Tertiary Solution (also can contain dissolved drug) |
|---|---|---|
| hydrocolloids | | |
| gelatin | | |
| gum tragacanth | | |
| carrageenans | | |
| karaya gum | | |
| guar gum | | |
| alginates | | |
| celluloses CMC, | | |
| CPC | | |
| phospholipids | | |
| lecithins | | |
| phosphatydl choline | | |
| Centrolex F | | |
| polysaccharides | | |
| corn starch | | |
| cyclodextrins | | |
| Oils (unsaturated or saturated) 1–10% | | |
| iodinated poppy seed oil (IPO) | | |
| mineral oil | | |
| cotton seed oil | | |
| olive oil | | |
| safflower oil | | |
| canola oil | | |
| peanut oil | | |
| sesame oil | | |
| corn oil | | |
| Dissolved Drugs 1% to saturation | | |

The formulations of the invention, in preferred embodiments, are less toxic than conventional liposomes and other microcapsules by avoiding use of certain phospholipids and long chain amines (eg. Stearylamine) contained in conventional microspheres which can produce toxic side effects.

Where the microcapsules of the invention comprise a pharmaceutical composition, certain medically related advantages may be obtained. Thus, due to the uniformity and ease with which the methods of the invention allow formation of multilamellar microcapsules, co-encapsulation of multiple drugs is made possible. Thus, for instance, as will be described more fully below, co-encapsulation of drugs and radiocontrast medium in the same microcapsules is made possible by the methods of the invention. Such co-encapsulation allows radiological monitoring of the tissue distribution during intravascular delivery. Additionally, incorporation of fluorescent-labels for entrapped drugs enables accurate measure of the drug compartment volumes (using fluorescent imaging techniques) and convenient determinations of the drug loading efficiencies, particle size distributions and measurement of shelf-life stability of the final parenteral suspensions. In some applications made possible by the methods and compositions of the invention, the organic phase can include a tracer compound or radiocontrast medium to provide the additional advantage of real-time imaging of the microcapsules with computerized tomography (CT) scanning as they are released from the catheter enroute to the target tissue. Other examples include aqueous soluble metallo-organic compounds used for diagnostic imaging such as ferrous gluconate or Gadolinium diethylene triamine pentaacetic acid (Gd-DTPA) used for nuclear magnetic resonance imaging and hydrocarbon soluble agents such as iron pentacarbonyl which also may be used for NMR imaging.

Production of multi-layered microcapsules via the methods of the invention which possess alternating hydrophobic and hydrophilic drug compartments allows for design of multiple-therapy microcapsules. Spontaneous formation of microcapsules with one or more large hydrophobic solvent compartments increases the potential application for delivery of more aqueous-insoluble drug at target sites with adequate vascular networks. By using the microcapsules made possible by the methods of the invention, sequential diffusion of two or more drugs out of the same microcapsule may be achieved at the target tissues. The incorporation of aqueous-soluble cyclodextrin which can act as an internal hydrophobic drug carrier is also made practical using the single step methods and formulations provided in this invention. This extends the capability of the invention in delivering otherwise aqueous-insoluble drugs.

For instance, the use of multiple drugs within the same microcapsule provides microcapsules specifically designed for chemoembolization treatments. Multiple-drug microcapsules also may be used to deliver first a chemotherapeutic drug which kills tumor cells, and then an immuno-adjuvant (tumor necrosis factor) or immunological stimulant (e.g. interferon-g) that would enhance the patient's immune response to the tumor. Multiple-drug microcapsules can also be used to deliver combinations of chemotherapeutic drugs to tumors that are located in privileged sites, such as brain tumors. For example, and as described more fully in the examples to follow, simultaneous delivery of different types of drugs in the same microcapsule is made possible with the methods and compositions of the invention, e.g. diaziquone and cis-platinum to brain tumors via the carotid artery [Kimier et al. 1993]. Multi-layered microcapsules may also be used to treat deep infections that are resistant to systemic antibiotics. In these applications, one or more antibiotics may be sequentially delivered to the site of the infection. Multi-layered microcapsules can be designed to protect active forms of urokinase and other thrombolytic enzymes until they are delivered and entrapped at the local site of a blood clot, where therapeutic doses of the enzyme may then diffuse out to dissolve the unwanted embolism. The multi-lamellar microcapsules can also be used to deliver immunostimulants; cytokines such as Interferons, Interleukins, and growth factors; antinauseants such as metoclopramide and tetrahydrocannabinol; multiple fibrinolytic enzymes such as urokinase (uPA), tissue plasminogen activator (tPA) and streptokinase; steroids such as hydrocortisone, dexamethasone, etc.; anti-fungals such as nystatin and griseofulvin, anti-virals such as amatidine, iododeoxuridine, riboviran; and multiple antibiotics such as amoxicillin, ampicillin, etc.

In one embodiment, as related to the space-based research that lead to the earth-normal embodiments of the invention, exposure to microgravity for at least 1.0 minutes in duration is accomplished. If the microcapsules of the invention are to be used in 1×g environments, as is generally anticipated, an additional step comprising recovering the multi-layer microcapsules will be necessarily accomplished at earth normal gravity. Generally, this step will be accomplished by reentry and recovery of the orbital device by which exposure to 0×g was accomplished. While it is preferred to accomplish the recovery without exposure of the formed microcapsules to physical extremes (pressure, temperature, shearing, mixing, etc.), recovery of the microcapsules of the invention have been accomplished via a transition from microgravity to earth normal gravity at accelerations of at least 15×g without substantial loss of integrity.

BRIEF DESCRIPTION OF THE DRAWINGS

FIG. 2A shows a typical result which fails to form microcapsules. FIG. 2B depicts certain best efforts to form microcapsules using prior art method.

FIG. 3A shows the typical result when the methods used under unit gravity.

FIG. 3B shows similar results when microcapsules are formed using the microgravity methods of the invention.

FIG. 6A shows a microcapsule with a single cubic crystal of Cis-Platinum trapped within. FIG. 6B shows a microcapsule with numerous crystals of Cis-Platinum formed within.

DESCRIPTION OF PREFERRED EMBODIMENTS

A series of more than 38 separate experiments on four space flights has led to the development of this invention. These experiments along with their ground-based counterparts are described below for the purpose of pointing out the invention specifically and providing details useful in carrying out the invention. These specific examples, however, do not limit the scope of the claimed invention.

Figure 1:
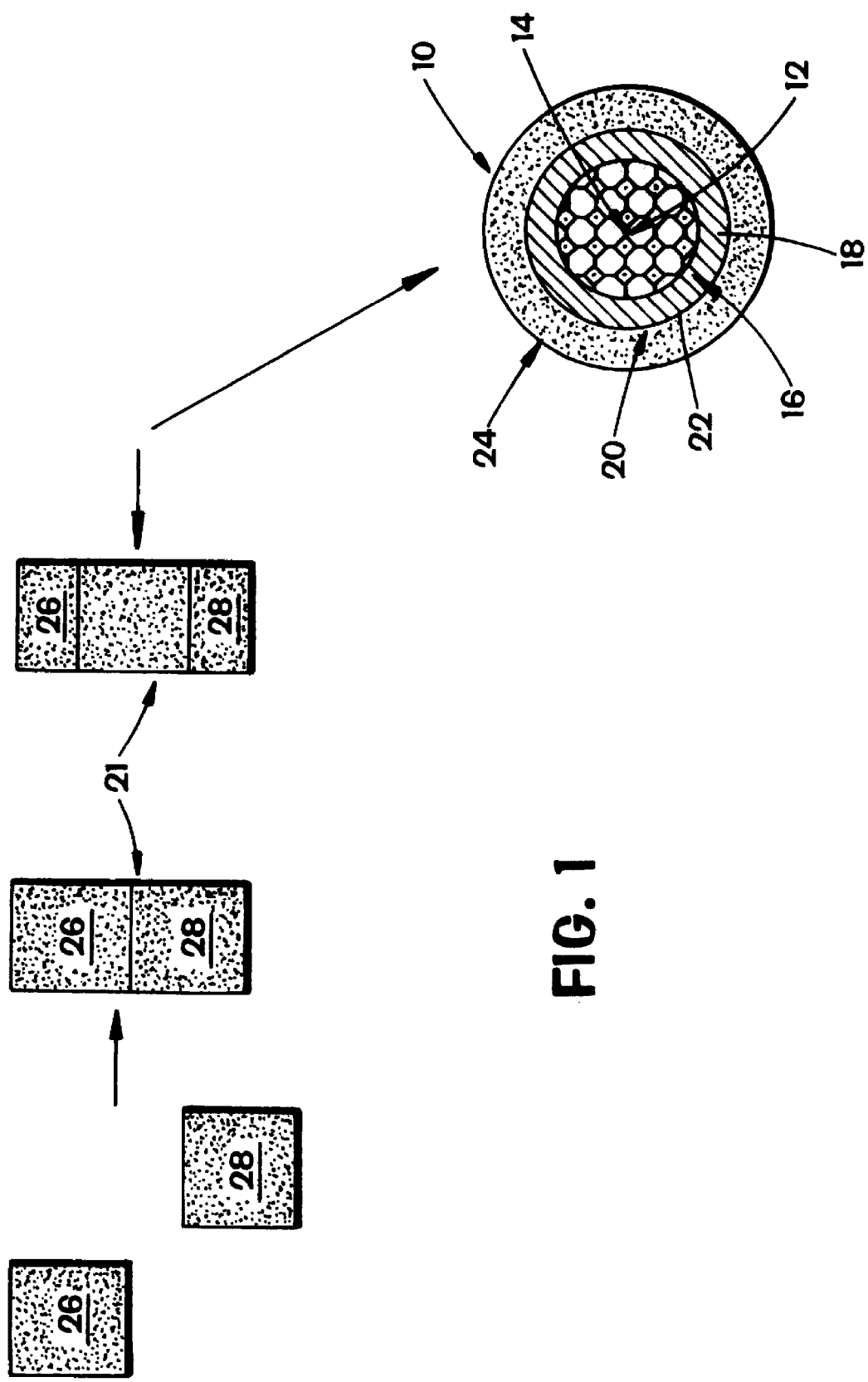
FIG. 1. Conceptual schematic showing formation of a multi-lamellar microcapsule with an aqueous drug/oil dispersion at its center, a hydrocarbon/oil drug #2 and/or radiocontrast medium (e.g. IPO) as a next layer, aqueous layer/drug (cis-platinum) as a next layer, and a polymer outer skin.

Referring first to the figures, FIG. 1 is a conceptual schematic showing formation of a multi-lamellar microcapsule 10 with an aqueous drug/oil dispersion 12 at its center 14, a hydrocarbon/oil drug#2 and/or radiocontrast medium (e.g. IPO) 16 as a next layer 18, an aqueous layer/drug (cis-platinum) 20 as a next layer 22, and a polymer outer skin 24. A first hydrocarbon phase 26 and a second aqueous phase 28, initially separated, are allowed to form an interface 21 with minimal mixing and low shear. If only diffusion-driven convection is allowed to occur at interface 21 thereafter, microcapsules of the invention form representative of that depicted 10.

Figure 2A:
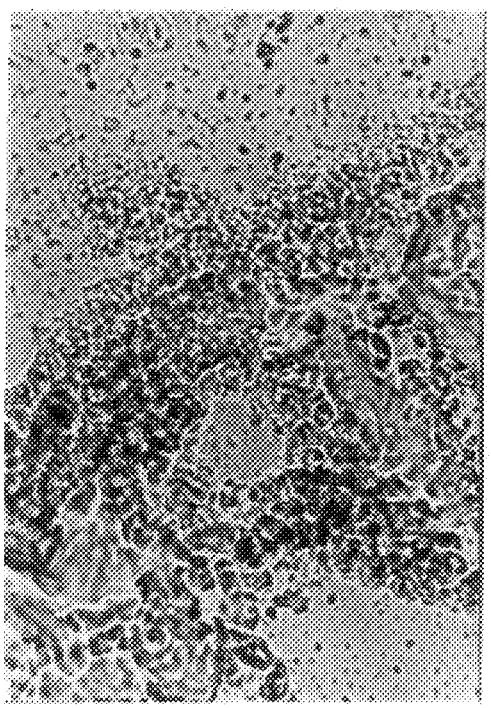
FIG. 2A and 2B. Photomicrographs of prior art method (vigorous mixing) to make microcapsules.
Figure 2B:
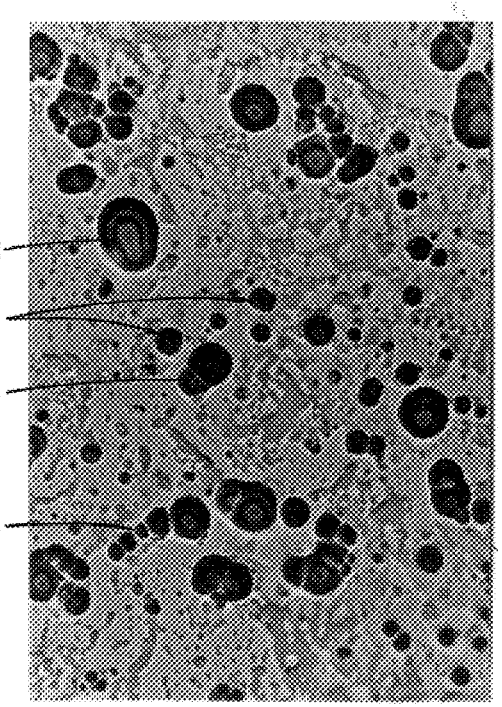

FIG. 2 is a pair of photomicrographs of the resulting mixture when a prior art method (utilizing vigorous mixing) is used with the preferred formulations of the invention to attempt to make microcapsules at earth normal gravity. FIG. 2A shows a typical result which fails to form microcapsules of any kind. FIG. 2B depicts certain best efforts to form microcapsules using this method. In FIG. 2B, in can be seen that certain poorly formed microcapsules 30 have formed. Typically, these microcapsules will demonstrate considerable lack of sphericity 32, coalescence 34, and non-uniformity 36.

Figure 3A:
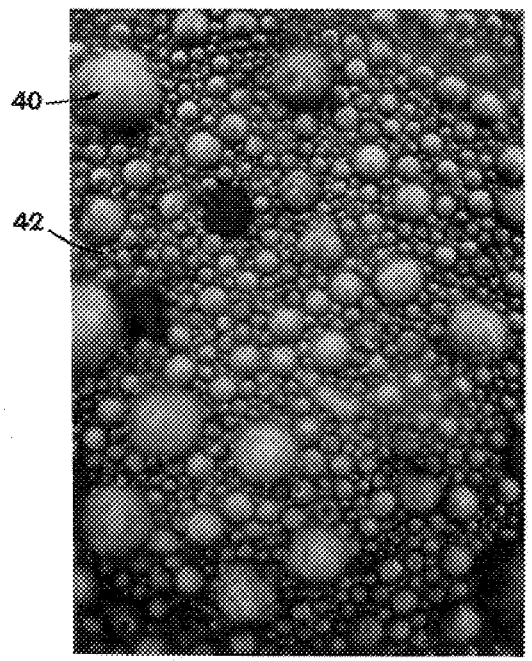
FIG. 3A and 3B. Photomicrographs depicting the distribution of sizes of microcapsules resulting from the methods of the invention are applied to form microcapsules.
Figure 3B:
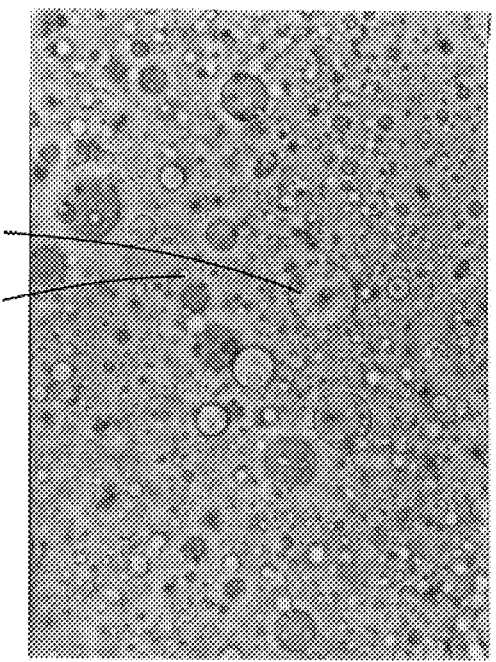

In FIG. 3, a pair of photomicrographs of the resulting mixture of when the methods of the invention are applied to form microcapsules. FIG. 3A shows the typical result when the methods of the invention are used to form microcapsules under unit gravity, at temperatures below ambient. Numerous microcapsules wherein the first phase is an organic phase formed, including certain ones of considerable diameter 40 as well as those of fairly small diameter 42. FIG. 3B shows similar results when microcapsules are formed using the microgravity methods of the invention using a first aqueous phase. Again, numerous microcapsules, including certain ones of considerable diameter 44 as well as those of fairly small diameter 46 form. It is clear from such photomicrographs, that uniformity and sphericity is a common characteristic of the microcapsules of the invention, regardless of the gravity environment.

Figure 4:
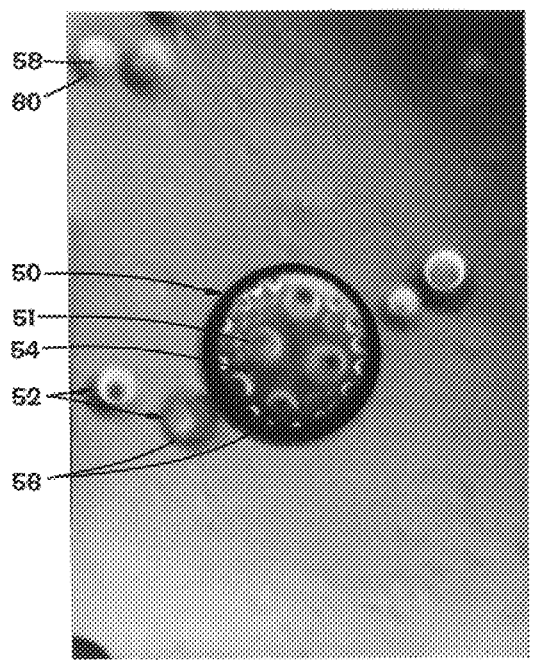
FIG. 4. Photomicrograph at enhanced magnification over that of FIG. 3A and B showing details of certain microcapsules of the invention.
Figure 5:
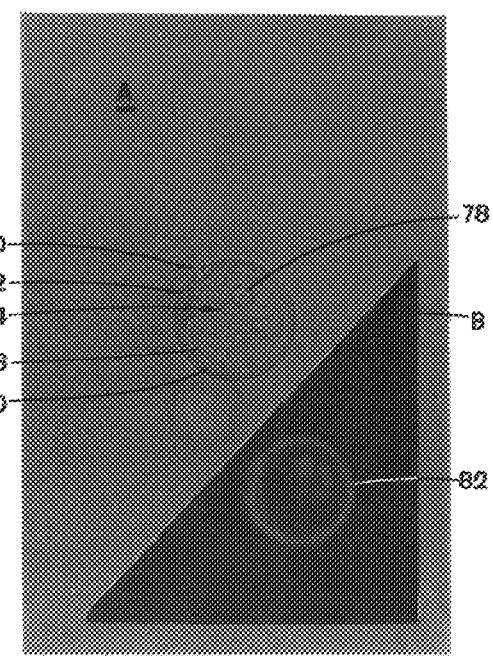
FIG. 5. Photomicrographs of a microcapsule of the invention which was made with a fluorescent dye. A shows a single microcapsule without using fluorescence microscopy. B shows the same microcapsule as photographed using fluorescence microscopy.

FIG. 4 is a photomicrograph at enhanced magnification over that of FIG. 3A and B showing details of certain microcapsules of the invention when practiced at unit gravity. A single large microcapsule 50 and several smaller ones 52 are shown. Nested inside microcapsule 50 can be seen several oil solvent spheroids (olive oil) 51 each of which is surrounded by the inner aqueous layer 54. A outer polymeric coating 56 can be seen on microcapsules 50 and 52. It is also possible to detect 3–4 spherical shells 58 nested within one another on certain of the smaller microcapsules 60. FIG. 5 is a photomicrograph of a microcapsule formed under microgravity of the invention which was made with a fluorescent dye in order to demonstrate the ability of the microcapsules of the invention to segregate a drug into a distinct layer. FIG. 5A shows a single microcapsule 70 in focus without using fluorescence microscopy comprising a outermost polymeric coating 72, an internal hydrocarbon solvent phase 74, a second polymeric membrane 76, aqueous spheroids 78 contained within the hydrocarbon inner layer 74, and an aqueous shell layer 80. FIG. 5B shows the result when the same microcapsule was photographed using a light source and optics to enable visualization of the fluorescent dye location, the internal spheroids 78 and aqueous shell or layer 80 are seen to fluoresce to indicate the location of the dye 82 therein.

Figure 6A:
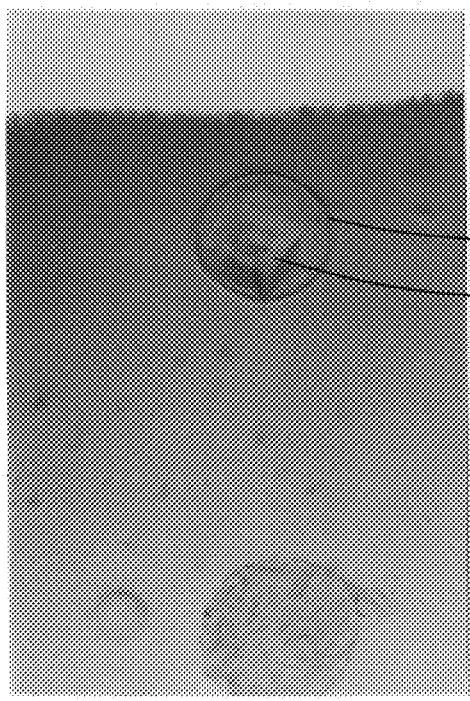
FIG. 6A and 6B. Microcapsules with crystalline structures in their internal layers or shells.
Figure 6B:
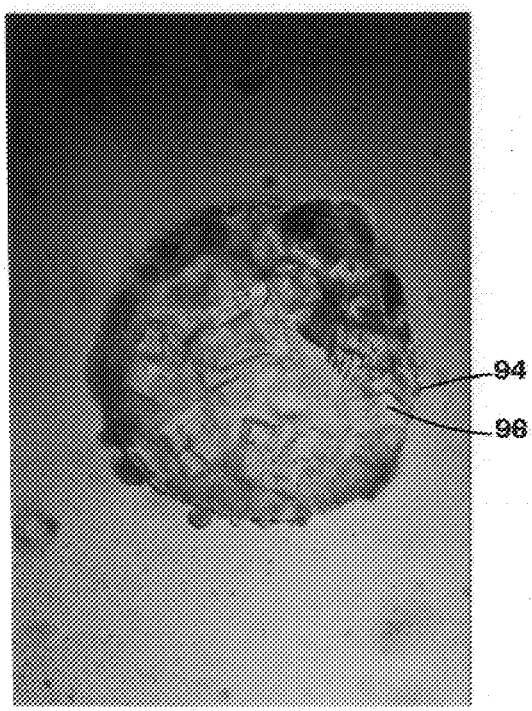

FIG. 6 depicts the capacity of the methods of the invention to create spherical microcapsules of uniform and substantial volumes which are capable of forming crystalline structures in their internal layers or shells. FIG. 6A shows a microcapsule 90 with a single cubic crystal of Cis-platinum 92 trapped within. FIG. 6B shows a microcapsule 94 with numerous crystals of Cis-Platinum 96 formed within.

Figure 7:
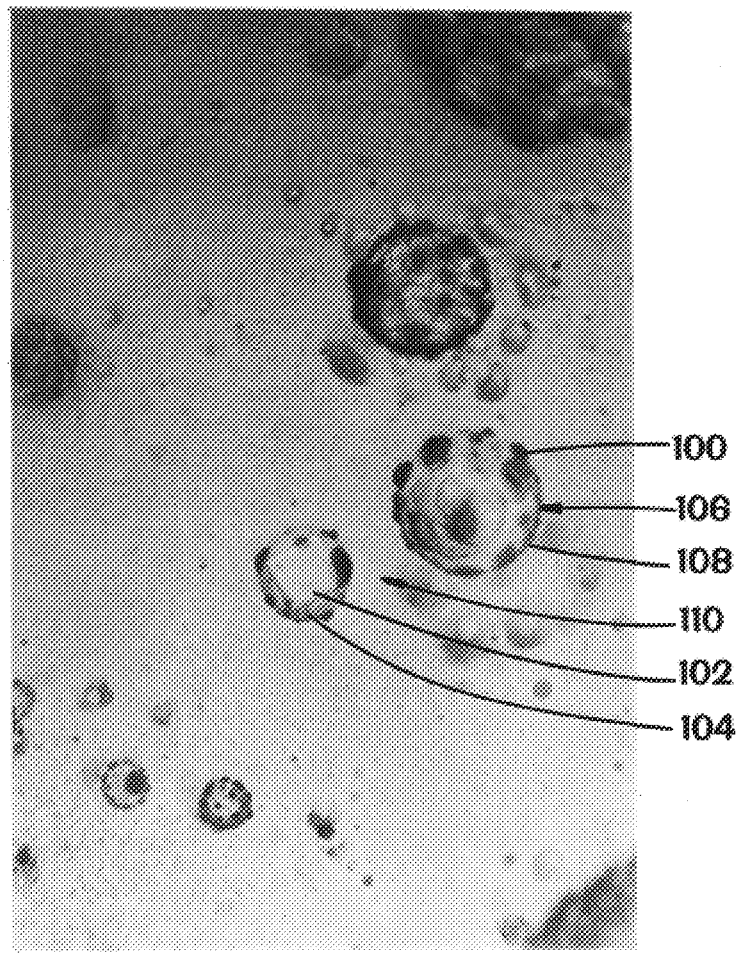
FIG. 7. Microcapsules which have been treated to contain a radio-contrast oil (iodinated poppy seed oil) and crystals of Cis-Platinum.

FIG. 7 shows a collection of microcapsules 110 of the invention which have been treated to contain a radio-contrast oil (iodinated poppy seed oil) 100 and crystals of Cis-Platinum 102 contained in microcapsules 104 with uniform spherical shells 106 and an outer polymeric coating 108.

EXAMPLE I

MICROGRAVITY EXPERIMENTS SUMMARY

The basic formulations and simplified liquid-liquid, dispersion methods were developed in 1988 and 1989. The conceptual approach is shown in FIG. 1. FIG. 1 is a schematic showing formation of a multi-lamellar microcapsule with an aqueous drug/oil dispersion at its center, a hydrocarbon/oil drug#2 and/or radiocontrast medium (e.g. IPO) as a next layer, an aqueous layer/drug (e.g., cis-platinum) as a next layer, and a polymeric outer coating or skin. Microencapsulation-related experiments designed to overcome the limitations of the first methods were conducted on six space missions beginning in April 1989 with the Consort-I sounding rocket using the Materials Dispersion Apparatus (MDA) mini-lab developed by Instrumentation Technology Associates, Inc. The sounding rocket flights produced only 6.5 minutes of microgravity conditions, but this was adequate to form the unique microcapsules in a single step. Experiments on the Space Shuttle permitted 10 minute dispersion times followed by curing of the outer polyglyceride skin for eight days under microgravity conditions. A summary of these experiments is shown in Table 2. New formulations were tested on Shuttle STS-52, using only aqueous-soluble drugs, polymers and surfactants, and on STS-56 using alcohols as co-surfactants. The specific experiments and results are described in detail in the examples to follow.

produced unique multi-lamellar microcapsules containing various aqueous drugs co-encapsulated with iodinated poppy seed oil (a radiocontrast medium with a sp. gravity= 1.35). Subsequent ground control experiments also produced some of these unique microcapsules and illustrated that the 1×g process could be improved to yield usable microcapsules by using different formulations. In particular, it became clear that the outer coatings substantially improved the ruggedness of the microcapsules formed.

EXAMPLE III

SOUNDING ROCKET EXPERIMENTS

Initial experiments on Consort-1 and -3 were used to determine the effective mixing and diffusion kinetics in the MDAs (see below for apparatus description). This showed that sufficient volume was mixed at the interface via diffusion to allow formation of microcapsules. These experiments also provided the diffusion constants for each of the components of the liquid phases.

TABLE 2

MED Flight Experiments Summary

| MISSION | [a]DATE | EXPERIMENTS | MATERIALS | RESULTS |
| --- | --- | --- | --- | --- |
| Consort-1 | 4/89 | protein diffusion | urokinase & antibodies | diffusion rates established |
| Consort-1 | 3/90 | diffusion kinetics | urokinase & myoglobin | kinetics verified |
| Consort-4 | 11/91 | microencap-sulation of drugs[ab] | Cis-Platinum, amoxicillin, urokinase & Strept-avidin | multi-lamellar microspheres w/ alternating hydrophilic & hydrophobic layers |
| Consort-5 | 9/92 | microencap-sulation of drugs[ab] | Cis-platinum, amoxicillin & urokinase | multi-lamellar microspheres w/ alternating hydrophilic & hydrophobic layers |
| STS-52 | 10/92 | microencap-sulation of drugs (aqueous polymers only)[ab] | Cis-platinum, amoxicillin & urokinase | multi-lamellar microspheres, crystals within microcapsules |
| STS-56 | 4/93 | microencap-sulation of drugs (alcohol co-surfactants)[ab] | Cis-platinum, amoxicillin & urokinase | multi-lamellar microspheres, crystals within microcapsules |

[a]Fluorescent labels included
[b]Fluorescent beads included

EXAMPLE II

GRAVITY-DEPENDENT RESTRICTIONS RECOGNIZED

Gravity-dependent restrictions in the basic liquid-liquid spontaneous microencapsulation process led to the design of several microgravity experiments to explore the utility of this process when density-driven phenomena were eliminated. In particular, density-driven, gravity-dependent restrictions of the liquid-liquid microencapsulation process were: early phase separation producing fragile microcapsules; interfacial dynamic flow causing coalescence of microcapsules. Failure of ground-based experiments to derive uniform microcapsules lead to a desire to attempt microcapsule formation in space.

The microgravity flight experiments led to the development of a new liquid-liquid microencapsulation process that involves use of surfactants and co-surfactants in the aqueous phase and co-surfactant alcohols in the organic phase, which also contained, in one embodiment, high molecular weight polymers that formed a tough outer "skin" on the final microcapsules. In microgravity, a single step dispersion The first successful microencapsulation of drugs in microgravity was conducted on the Consort-4 mission in Nov. 1991. The microcapsules were recovered and analyzed by microscopic image analysis. Mono-dispersed fluorescent beads were included as internal size standards and fluorescent labels were used to determine the distribution of drug in the various fluid compartments. Additional experiments, conducted on Consort-5 in September 1992, confirmed the capabilities of the new method for forming multi-lamellar microcapsules with alternating layers of hydrophilic and hydrophobic drugs.

Microcapsules formed in 38 microgravity mini-experiments used liquid-liquid dispersion of aqueous drug solutions, surfactant and polyethylene glycol dispersed in alcoholic co-surfactant solutions containing soluble polyglycerides.

Microcapsules of both oil/water and polymer/water/oil were recovered from the Consort flights. These experiments produced multi-lamellar liquid microcapsules (concentric spheres within spheres) comprised of three or more, alternating immiscible layers. Image analysis of the microcapsules was made possible by co-encapsulation of standard size fluorescent beads. Microcapsules were formed in the ranges of 1–15 microns, 40–50 microns, 110–130 microns and 160–230 microns in diameters. This was a substantial improvement over the prior art approaches which had initially been attempted by the inventors to derive microcapsules only in the 10 micron and less-range. The size distribution covered a range of from about as low as 5 microns in diameter up to about 300 microns in diameter and greater. The average size of the microcapsules formed in these experiments was about 150 microns, greatly in excess of the average 10 micron or less diameters obtained with prior art approaches.

The ruggedness of the microcapsules formed under these conditions allowed for size segregation by sieving. Digital analysis (National Institutes of Health image analysis program) of phase contrast and fluorescent images taken with a fluorescent microscope also confirmed that the aqueous-soluble drugs were routinely encapsulated within the inner aqueous core and the outermost aqueous shell of the microcapsules.

This typical distribution is illustrated in FIG. 5, which is a composite of a transmitted light photomicrograph and a fluorescent photomicrograph (lower right) of the same multi-lamellar microcapsule. The polyglyceride skin is clearly shown in the normal-light photomicrograph (upper left).

Multi-lamellar microcapsules were, also formed which contained relatively large amounts of IPO (Guerbet Laboratories - France, Savage Laboratories - U.S.A.) in discrete lamella. FIG. 7 shows a microcapsule heavily loaded with IPO, which often comprised up to 38% of the total volume. Often small hemispheres of IPO were also found clinging to the outer surface of the large inner (aqueous) sphere or adhered to the outer polymer skin of the microcapsule.

Microcapsules formed by almost all of the formulations survived 15+g accelerations, severe vibrations and turbulent mixing, during the reentry of the experiment capsule, and have remained intact for two years after recovery from space. These multi-layered microcapsules are similar to liquid-filled, thin-skinned, micro-balloons which are flexible enough to be manipulated on a microscope slide without collapse.

The microcapsules formed in just 6.5 minutes of microgravity retain their spherical shape and appear tough enough to survive the extensive physical manipulations required for sizing, final preparation and storage of parenteral suspensions, and the fluid shear encountered after intravascular injection.

Also formed were very unusual structures (multiple small spheres of aqueous-soluble drug) distributed within multi-lamellar o/w/o microcapsules, wherein the aqueous spheroids are arranged in an annular ring that appears fixed in a plane within the innermost sphere (not shown). These ring structures remain intact when the microcapsules are "rolled around" on the microscope slide without rupturing. These structures demonstrate the ability of the methods of the invention to form small spheroids that do not coalesce inside the larger microcapsule. Such structures may be advantageously used to control the specific volume to surface area ratio in order to control the rate of diffusion of a solute in such spheroids. In particular, sustained release of pharmaceuticals contained in such spheroids within microcapsules may find utility.

EXAMPLE IV

SPACE SHUTTLE EXPERIMENTS

Microencapsulation experiments on Consort 4 and Consort 5 used mixtures of aqueous-soluble drugs, IPO, C3–C8 alcohols and polyglycerides that are insoluble in aqueous solutions. In experiments conducted on STS-52, the inventors co-encapsulated cis-platinum (diaminodichlor-cis-platinum; Bristol Laboratories) with IPO by forming microcapsules from water-soluble polymers using special formulations of aqueous, non-alcoholic solvents. Such formulations will find particular utility in co-encapsulations of anti-tumor compounds along with radiocontrast medium for tracking drugs in the body.

Polyvinyl pyrolidone (PVP) and a commercial lethicin (Centrolex-F™; a lecithins compound produced by U.S. Soya, Inc.) were used to form multi-lamellar microcapsules at 20° C. Fluorescent beads and fluorescent labeled were co-encapsulated with the drugs to permit drug-distribution measurements, within the various lamellae, using fluorescence microscopy and digital image analysis at the NASA Johnson Space Center, Houston, Tex. The final microcapsules were suspended and recovered in either aqueous solutions, IPO or mineral oil. The microcapsules formed by these formulations were similar to those made using alcohol-soluble polyglycerides. However, without the hydrocarbon-soluble polyglyceride skin these microcapsules were more fragile.

Another unique type of microcapsule was formed during these experiments that was characterized by drug crystals formed within the inner aqueous core of the multi-lamellar microcapsules. FIG. 6B shows an example of a microcapsule which is packed (approximately 65% of the aqueous compartment) with crystals of Cis-platinum, an anti-tumor drug. Microcapsules containing crystals of amoxicillin were also formed in the STS-52 experiments (not shown). These illustrate that aqueous-soluble drugs can be encapsulated at very high concentrations near the solubility limit of the drug. After the microcapsules are formed the drug can become further concentrated (perhaps via the alcohol absorbing the water from the aqueous phase in which the pharmaceutical solute is dissolved) to form large crystals which are more stable than the dissolved drug during prolonged storage.

Microcapsules formed from first organic solvent/polymer methods appeared to be more rugged (by visual comparison under the microscope) than those formed on STS-52 formed from first solvent aqueous/polymer methods. The STS-56 experiments again produced multi-lamellar liquid microcapsules (multiple concentric spheres within spheres) comprised of alternating immiscible layers. Using fluorescent 6.4 micron beads and image analysis, it was found that the most interesting microcapsules were formed in the range of 10–15 micron, 40–50 micron, 50–100 micron, and 160–230 micron diameters. These diameter distributions were of particular interest since it is known that intraarterial uses can accommodate 50–300 micron diameter microcapsules while intravenous applications can only tolerate 1–10 micron microcapsules. Thus, by segregating the microcapsules into sized fractions (sieving), it should be possible to address particular intravascular limitations.

As noted above, microcapsules were formed containing crystals of cis-Platinum or amoxicillin. The crystals apparently were formed after encapsulation. Several microcapsules were formed that contained a single, large cubic crystal of Cis-Platinum which so completely filled the inner sphere that only about 15% of the inner volume remained as a liquid. One encapsulated, cubic Cis-Platinum crystal was measured at $48\mu$ across within a $57\mu$ diameter microcapsule (similar to that shown in FIG. 6A). After formation, some of the microcapsules were dispersed in an external oil phase (either IPO or mineral oil) and allowed to cure for eight days before return to Earth.

These microgravity experiments have shown that formation of multi-lamellar, alternating-phase microcapsules can be controlled by proper timed-sequence exposures of the immiscible phases using special solvent formulations and surfactants. Once formed, these microcapsules remain spherical due to the predominant surface tension of the internal phases and polymer/solvent phase partitioning at the interfaces.

These experiments clearly demonstrated the capability to use liquid-liquid diffusion mixing to form unique microcapsules containing hydrophilic and hydrophobic drugs under microgravity conditions. Thus, ground-based experiments were conducted to compliment and replicate the space experiments. These ground-based experiments were able to replicate the size range (5–250 microns in diameter) to a limited degree, but the average size microcapsule obtained was about 10–40 microns in diameter. Still, this was a substantial improvement over the prior art approaches which rarely formed microcapsules over 10 microns in diameter. It was also observed that the ground-based experiments resulted in less rugged microcapsules. This is likely a result of the gravity-dependent deformations of the spherical microcapsules as they form giving rise to areas of thinner polymer deposition. Thus, the flexible microcapsules, formed under microgravity conditions, have more uniform size distributions than those formed in 1×g, are more rugged, and have a higher average diameter than ground-made microcapsules, largely due to the absence of thermal convection, buoyancy forces, and instabilities that occur at the immiscible interfaces.

The microgravity experiments illustrate the feasibility of co-encapsulating aqueous-soluble drugs, hydrocarbon-soluble drugs and oil-based contrast media within a lipid-soluble, polyglyceride outer film which cures rapidly enough to be impervious to oil or hydrocarbon resolubilization. They also allow the formation and harvesting of unique microcapsules which are durable enough to be removed from the external solvent without disruption or destruction of the internal phases. It is anticipated that these microcapsules will have several advantages over conventional liposomes that are designed for intravascular injection.

EXAMPLE V

FLIGHT HARDWARE DESCRIPTION

The microencapsulation experiments described herein were conducted using the Materials Dispersion Apparatus (MDA; ITA, Inc., Exton, Pa.). The MDA's consist of an upper and a lower block that contain chambers for each sample fluid. The blocks are misaligned at launch so that the chambers are not in contact with each other. Upon activation in microgravity, the blocks are moved to align the chambers so that the fluids, can mix by liquid-liquid diffusion. Some of the experiments were conducted with a single-step fluid mixing, and some were done with a two-step fluid mixing technique which allows diffusion of a third fluid or sample into the mixture of the first two fluids while still in the microgravity environment.

EXAMPLE VI

DISCUSSION AND ALTERNATIVE EMBODIMENTS

Spontaneous formation of multi-lamellar, microcapsules containing alternating layers of aqueous and hydrophobic solvent compartments is strongly dependent on the interfacial tension and the amount of mixing between immiscible liquid phases. On Earth this process is limited by gravity-dependent, density-driven separation of the immiscible liquids into stratified horizontal layers. In microgravity, this process is largely dependent on the surface-free energies of the different liquids, but independent of density-driven convection or buoyant phase separation. Hydrocarbon soluble, high molecular weight polymers have been included in the formulations to form flexible, permeable "skins" or outer coatings around the liquid microcapsules as they are created by phase partitioning mechanisms. It is also possible to form such polymer barriers between internal layers. The microcapsules can be formed and cured without deformation by contact with container walls.

More specifically, co-encapsulation of an aqueous-soluble, anti-tumor drug (Cis-platinum) and a radio-contrast medium (IPO), in microgravity, has produced a unique drug delivery system that can be visualized by radiologic or computerized tomography scanning to insure that the cytotoxic drug is delivered directly to the target tumor. Multi-layered microcapsules have been developed which can provide a new intravascular delivery system for targeted tissues and sequential, sustained release of multiple anti-tumor drugs. This method has resulted in formation of flexible spherical microcapsules of more uniform sizes, which can provide maximum packing densities and maximum drug delivery to target organs or tumors.

Multi-layered microcapsules can be designed to protect active forms of urokinase and other thrombolytic enzymes until they are delivered and entrapped at the local site of a blood clot, where therapeutic doses of the enzyme can diffuse out to dissolve the unwanted embolism. These immiscible-liquid diffusion methods also could be used for encapsulating certain labile drugs to make microcapsules for special purpose drug delivery systems, especially those designed to deliver drugs via the nasal or buccal mucosa or via inhalation directly to the lungs. Examples include protected delivery of mucolytic DNAse for sustained release treatment of cystic fibrosis and α anti-trypsin for patients with deficiencies in the lung epithelium.

EXAMPLE VIII

REDISPERSION OF MICROCAPSULES IN AQUEOUS OR OIL VEHICLES

A frequently used second step includes dispersion of the microcapsules (after they have formed) in different aqueous/polymer solvents or in a pure oil phase. A unique attribute of microcapsules formed by these methods is that they do not re-dissolve in an oily external phase, even though the semi-permeable outer skin is hydrophobic. This produces a suspension in the liquid carriers that are commonly used for,intravascular administration.

EXAMPLE IX

EXEMPLARY FIRST ORGANIC SOLVENT MICROCAPSULE FORMULATIONS

The following formulations have been used with particular success by the inventors in both earth normal and microgravity methods of making microcapsules.

Fluid 1—(hydrocarbon)

The first solvent is a hydrocarbon fluid (ethyl alcohol, methyl alcohol, or isopropyl alcohol) with a low or medium HLB (HLB=5–10). One or more co-solvents are used (which also can act as co-surfactants). Small concentrations of oil and water are added. Into this mixture, the mono- or polyglyceride is dissolved up to 5% w/v. An example is:

88% IPA 2.5% m-Hexanol 2.5% n-Heptanol

5% IPO

2% $H_2O$

5% GMS

Fluid 2 (aqueous)

The second solvent is water plus surfactants (ex. polyethoxylated sorbitan esters; polyethylene glycol). A polysaccharide (Dextran) and normal saline (0.9%) are added which helps achieve the desired critical micelle concentration. A pharmaceutical soluble in water is added. An example is:

1% PEG 4000

5% Dextran-40 (MW=40,000)

0.9% Sodium chloride

2% Sorbitan Monooleate/20 moles Ethylene oxide

Water (up to 100% volume)

dissolved drug at specified concentration (according to required dose and release rate)

Fluid 3 (oil)

An oil, immiscible with the first two fluids in which the microcapsule's "outer skin" is insoluble so that the suspended microcapsules can be delivered by injection when non-aqueous administration is required. Submersion of microcapsules in the oil also can aid the curing or polymerization of the "outer skin." A preferred example of the oil vehicle is iodinated poppy seed oil which also serves as a radiocontrast medium.

Alternate compositions for Fluid 1

Main solvent—ethyl alcohol

Co-solvents—(co-surfactants) are normal alcohols—C4 to C8 high dielectric constant solvents
  tetrahydrofuran
  dioxane
  acetonitrile
  dimethylformamide
  dimethylacetamide
  dimethylsulfoxide Oil—dense radiocontrast liquids s.a. iodinated unsaturated oils
  e.g. poppy seed oil, cotton seed oil, safflower oil, olive oil, canola oil, peanut oil, sesame oil, corn oil.
  also saturated oils can be used, s.a. heavy mineral oil, liquid petrolatum Polymers—used to form the "outer skin" on the microcapsules monoglycerides—esp. glycerol esters ranging from C12–C22,
  e.g. monostearate, distearates, monooleates, monolaurates and olive oil polyglycerides—cholesterol, waxy plant sterols (stigmasterol, phytosterol, campesterol) phospholipids—lecithins (phosphatidyl choline) and/or combinations with mono/polyglycerides

| Alternate concentrations: | | |
|---|---|---|
| Fluid 1: | Main solvent | 75–95% |
| | Co-solvents | 1–10% |
| | Oil | 1–10% |
| | Polymer | 1–5% |
| | Water | 1–20% |

Alternate composition for Fluid 2

PEG 200–10000

Dextran-40 (MW=40,000–70,000)

0.9% Sodium chloride

Sorbitan Monolaurate/20 moles Ethylene oxide balance is water

Drug dissolved at saturated or specified concentration
  (according to required dose and release rate)

| Alternate concentrations: | |
|---|---|
| PEG | 1–5% |
| Dextran (MW = 40,000–70,000) | 5–10% |
| Sodium chloride | 0.9% |
| Sorbitan Monolaurate/20ETO | 1–5% |
| Water (balance of volume) | |
| Drug concentration saturated or specified | |

Alternate composition for Fluid 3 (Oils)

Dense radiocontrast liquids s.a. iodinated unsaturated oils e.g. poppy seed oil, cotton seed oil, safflower oil, olive oil, canola oil, peanut oil, sesame oil, corn oil.

Also saturated oils can be used, s.a. heavy mineral oil

Alternate concentrations

100% oil or a mixture is used as a carrier vehicle for the suspended microcapsules

EXAMPLE X

EXEMPLARY FIRST AQUEOUS SOLVENT MICROCAPSULE FORMULATIONS

ALTERNATE METHOD—Hydrophilic Outer Skin

Fluid 1—(aqueous); the main solvent is a water, one or more co-solvents (which also can act as co-surfactants), and a lecithins is dissolved up to 5% w/v to form the outer skin on the microcapsules.

An example is:

3% polyvinyl alcohol dissolved in a mixture of

20% isopropyl alcohol and

80% water

Fluid 2 (aqueous); the main solvent is water plus surfactants (ex. polyethoxylated sorbitan esters; polyethylene glycol) and plus a polysaccharide (Dextran) and normal saline (0.9%) which helps achieve the desired critical micelle concentration.

An example is:

1% PEG 4000

5% Dextran-70 (MW=~70,000)

0.9% Sodium chloride

2% Sorbitan Monooleate/20 moles Ethylene oxide

Water (up to 100% volume)

dissolved drug at saturated or specified concentration
(according to required dose and release rate)
Fluid 3 (aqueous)—a PEG and PVP solution which can aid the curing or polymerization of the "louter skin."

1% Polyvinyl pyrolidone

4% PEG 4000

5% Dextran-70 (MW=~70,000)

balance is 0.9% Sodium chloride

REFERENCES CITED

The following references to the extent that they provide details supplementary to those set forth herein, are specifically incorporated herein by reference.

Allen, T. M.. Interactions of Drug Carriers with the Mononuclear Phagocytic System, in G. Gregoriadis (Ed.) *Liposomes as Drug Carriers*, John Wiley & Sons Ltd., New York, pp.37–50, 1988.

Allen, T. M., Mehra, T., Hansen, C. and Chin, Y. C., Stealth Liposomes: An Improved Sustained Release System for 1-b-D-Arabinofuranosylcytosine, Cancer Res. 52:2431–39, 1992.

Bhargava, H. N., Narurkar, A., and Lieb, L. M., Using Microemulsions for Drug Delivery, Pharmaceutical Technology, pp. 46–54, Mar. 1987.

Gabizon, A., et al., Liposome-Associated Doxorubicin: Preclinical Pharmacology and Exploratory Clinical Phase, in G. Lopez-Berestein and I. J. Fidler (Eds.) *Therapy of Infectious Diseases and Cancer*, Alan R. Liss, Inc., New York, pp. 189-203, 1992.

Halbert, G. W. , Stuart, J. B., Florence, A. T., The Incorporation of Lipid Soluble Antineoplastic Agents into Microemulsions-Protein-free Analogues of Low Density Lipoprotein, Int. J. Pharm. 21: 219–232, 1984.

Kimler, B. F, et al., Combination of Aziridinylbenzoquinone and Cis-platinum with Radiation Therapy in the 9L Rat Brain Tumor Model, Int. J. Radiation Oncology Biol. Phys, 26: 445–450, 1993.

McCutcheon's Detergents and Emulsifiers, 1979, North American Edition, McCutcheon Division, MC Publishing Co., 175 Rock Road, Glen Rock, N.J. 07452. "Specifically, for HLB values ranging from 2 to 42 , see pages 29–39, and for HLB values ranging from 0.5 to 30.5, see pages 228–241."

Parikl, 1. and Stern, W. Microcrystal™ Drug Delivery System, in Harvey S. Price (Ed) The Biotechnology Report 1993/94, Bookbuilders, Ltd., Hong Kong, pp. 219–220, 1994.

Talsma, H. and Crommelin, D. J. A., Liposomes as Drug Delivery Systems, Part 1: Preparation. Pharmaceutical Technology, pp. 96–106, October 1992.

Wright, K. C., Wallace, S., Mosier, B. and Mosier, D., Microcapsules for Arterial Chemoembolization: Appearance and In Vitro Drug Release Characteristics, J. Microencapsulation 5:13–20, 1988.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, one alternate embodiment includes use of aqueous-soluble cyclodextrin (in the hydrophilic phase) which has hydrophobic center that can itself entrap hydrophobic drugs,thereby acting as a carrier for hydrophobic drugs within the aqueous phase. Another alternate embodiment allows after microcapsules are formed, for ancillary polymeric outer coats to be applied by conventional methods (electrostatic coating, aerosolization and drying, etc.). This is made possible by designing the precise chemical makeup of the initial polymeric outer skin such that it will be compatible with both drug diffusion and the ancillary coating to be applied. When surfactants are used to facilitate adhesion of the third solution or ancillary coating the HLB must be selected to be compatible with the HLB of the existing outer coating which has already been formed, such that the solution containing the ancillary coating will wet the surface of the existing outer coating, to enable deposition of the ancillary coating. This is in contrast to conventional liposomes whose outer membrane composition is a variable, depending on the phase separation of the phospholipids and cholesterol adduct when each liposome forms. Another alternative embodiment incorporates an energy absorbing medium ( e.g. photoactivator) which can absorb electromagnetic, ultraviolet, infrared, ultrasonic, radiofrequency and microwave radiation and thereby cause activation of a short-lived drug component just prior to administration or after the microcapsules have reached the target site. Another embodiment incorporates magnetic particles and magnetic fields or free-fluid electrophoretic mechanisms, etc. to facilitate dispersion or transport of one phase across the immiscible interface into the other phase. This has been demonstrated as a single pass, uni-directional form of mixing that is best exploited in microgravity. Another embodiment includes attachment of certain (hydrophobic) antibodies to the polymeric skin which gives the microcapsules site specificity by being able to bind to target cells (e.g. tumor) while entrapped drugs diffuse out to provide maximum doses to those cells with that antigenic site. Another embodiment makes use of polyethylene glycol (PEG) complexed to peptide or protein drugs and a customized polymeric outer skin which permits the drug-PEG complex to diffuse out of the microcapsule as an intact entity. This permits the drug to resist antibody attachment and remain in the blood stream longer as found in the Pegnology$^{SM}$ type of drug complexes developed by Enzon, Inc. The improvement being delivery of this complex in the tailored microcapsules and controlled release of the complex through the specially designed polymeric outer skin. All such modifications are intended to be included within the scope of the appended claims.

What is claimed is:

1. A method of making a multi-layered microcapsule, comprising:

formulating a first phase comprising a first solvent, a first microcapsule layer-forming compound soluble in said first phase and immiscible in a second phase, a co-solvent, oil, and water;

formulating said second phase immiscible with said first phase, said second phase comprising a second solvent, a second microcapsule layer-forming compound soluble in said second phase and immiscible in said first phase, a surface active agent, and a salt;

said surface active agent having a hydrophilic/lipophilic balance value greater than that of said first microcapsule layer-forming compound;

said second microcapsule layer-forming compound having a hydrophilic/lipophilic balance value lower than that of said surface active agent;

creating an interface between said first and second phases in a manner that limits fluid shear equal to or less than about 12 dynes/cm$^2$ , and maintains adsorptive surface characteristics at said interface.

2. The method of claim 1 wherein said first solvent is organic.

3. The method of claim 2 wherein said organic solvent is selected from the group of organic solvents consisting of methyl alcohol, ethyl alcohol, and isopropyl alcohol.

4. The method of claim 1 wherein said first microcapsule layer-forming compound is selected from the group consisting of glycerol monosterate, glycerol monooleate, glycerol monolaurate, glycerol dioleate, glycerol distearate, cholesterol, stigmasterol, phytosterol, campesterol, polyvinyl pyrrolidone, polyvinyl alcohols, hydrocolloids, and lecithins.

5. The method of claim 1 wherein said first solvent is aqueous.

6. The method of claim 4 wherein said hydrocolloid is selected from the group of hydrocolloids consisting of gelatin, gum tragacanth, carrageenan, Karaya gum, Guar gum, gum arabic, alginates, carboxymethyl cellulose, hydroxypropyl cellulose, and carboxypropyl cellulose.

7. The method of claim 1, said first phase further comprising a co-solvent, wherein said co-solvent is selected from the group of co-solvents consisting of $C_3$–$C_8$ alcohols, tetrahydrofuran, dioxane, acetonitrile, dimethylformamide, dimethylacetamide, and dimethyl sulfoxide.

8. The method of claim 1 wherein said oil is selected from the group of oils consisting of poppy seed oil, olive oil, peanut oil, sesame oil, cotton seed oil, soybean oil, safflower oil, corn oil, sunflower seed oil, canola oil, mineral oil, $C_{20}$–$C_{38}$ paraffinic oil, and liquid petrolatum.

9. The method of claim 1 wherein said oil is an unsaturated oil which has been halogenated.

10. The method of claim 1 wherein said second microcapsule layer-forming compound is selected from the group consisting of polyethyleneglycol, polyvinylpyrrolidone, polyvinyl alcohols, and hydrocolloids.

11. The method of claim 1 wherein said surface active agent has a hydrophilic/lipophilic balance value of about 10.0 or greater.

12. The method of claim 11 wherein said surface active agent is selected from the group of surface active agents consisting of sorbitan monooleate treated with ethylene oxide, dextran, polyethylene glycol, $C_{12}$–$C_{20}$ fatty acids, 2-amino-2-methyl-1-propyl aminomethyl propanol amphoteric salts, and quaternary ammonium salts.

13. The method of claim 1 wherein said salt is selected from the group of salts consisting of NaCl, KCl, $CaCl_2$, $MgCl_2$, quaternary ammonium salts, cetyl trimethylammonium bromide, and 4-methoxy-4(3-phosphatidyl choline) spiro(1,2-dioxetane-3-g,1-adamantane) disodium salt.

14. The method of claim 1 wherein said first phase further comprises a pharmaceutical composition.

15. The method of claim 14 wherein said pharmaceutical composition is selected from the group of pharmaceutical compositions consisting of cytotoxins, proteases, cytokines, anti-nauseants, steroids, anti-fungal agents, fibrinolytic enzymes, and antibiotics.

16. The method of claim 14 wherein said pharmaceutical composition is in suspension.

17. The method of claim 1 wherein said second phase further comprises a pharmaceutical composition.

18. The method of claim 17 wherein said pharmaceutical composition is selected from the group of pharmaceutical compositions consisting of cytotoxins, proteases, cytokines, anti-nauseants, steroids, anti-fungal agents, fibrinolytic enzymes, and antibiotics.

19. The method of claim 17 wherein said pharmaceutical composition is in suspension.

20. The method of claim 14 wherein said pharmaceutical is at a concentration sufficient to allow nascent crystal formation within said microcapsule.

21. The method of claim 1, wherein after said microcapsule forms, taking additional steps comprising:
   formulating a third phase comprising an oil or $C_{20}$–$C_{38}$ paraffin; and,
   contacting said microcapsule with said third phase.

22. The method of claim 21, wherein said third phase further comprises a polymer.

23. The method of claim 21, wherein said third phase further comprises a pharmaceutical composition.

24. The method of claim 1, wherein after said microcapsule forms, taking additional steps comprising:
   formulating a third phase comprising an aqueous solution; and,
   contacting said microcapsule with said third phase.

25. The method of claim 24, wherein said third phase further comprises a pharmaceutical composition.

26. The method of claim 24, wherein said third phase further comprises an adjuvant.

27. The method of claim 24, wherein said third phase further comprises an activator agent.

28. The method of claim 26, wherein said adjuvant further comprises an immunoglobulin, peptide, protein, hydrocolloid or polysaccharide.

29. The method of claim 28, wherein said hydrocolloid is selected from the group of such hydrocolloids consisting of collagen, isoelectric gelatin, agar, gum arabic, gum tragacanth, carboxymethylcellulose (CMS), carboxymethyl/ethyl cellulose (CMEC), hydroxyethylcellulose (HEC), hydroxymethyl/ethyl cellulose (HMEC), hydroxypropyl cellulose (HPC), alginates and carrageenans.

30. The method of claim 24, wherein said third phase further comprises a surface active agent compatible with the hydrophilic/lipophilic balance value of an outer coating of said microcapsule.

31. The method of claim 1 wherein one or more of said phases further comprise fluorescent molecules selected from the group of fluorescent molecules consisting of fluoresceins, cyanins, naturally fluorescent molecules, and rhodamines.

32. The method of claim 1 wherein said adsorptive surface characteristics comprise a Helmholtz charge distribution at said interface.

33. The method of claim 1 wherein said maintenance of adsorptive surface characteristics is promoted by carrying out the method under microgravity of less than or about equal to $1 \times 10^{-2}$g and with fluid shear of no more than between about 2–12 dynes/cm$^2$.

34. The method of claim 33 wherein said microgravity is at least 1.0 minute in duration.

35. The method of claim 1 wherein said maintenance of adsorptive surface characteristics is promoted by carrying out the method below ambient temperature.

36. The method of claim 1 wherein said maintenance of adsorptive surface characteristics is promoted by substantially balancing the specific gravity between said phases.

37. A method of making a multi-layered microcapsule, comprising:
   formulating a first phase comprising an organic solvent selected from the group of organic solvents consisting of methyl alcohol, ethyl alcohol and isopropyl alcohol, a first microcapsule layer-forming compound soluble in said first phase selected from the group of polymers consisting of glycerol monosterate, glycerol monooleate, glycerol monolaurate, glycerol dioleate, glycerol distearate, cholesterol, stigmasterol, phytosterol, campesterol, and lecithins, a co-solvent selected from the group of co-solvents consisting of $C_3$–$C_8$ alcohols, tetrahydrofuran, dioxane, acetonitrile, dimethylformamide, dimethylacetamide, and dimethyl sulfoxide, an oil selected from the group of oils consisting of poppy seed oil, olive oil, peanut oil, sesame oil, cotton seed oil, soybean oil, safflower oil, corn oil, sunflower seed oil, canola oil, mineral oil, $C_{20}$–$C_{28}$ paraffinic oil, liquid petrolatum, and water;

formulating a second phase immiscible with said first phase, said second phase comprising water, a second microcapsule layer-forming compound soluble in said second phase selected from the group consisting of polyethyleneglycol, dextran, polyvinylpyrrolidone, polyvinyl alcohols, hydrocolloids, and lecithins, a surface active agent selected from the group consisting of sorbitan monooleate treated with ethylene oxide, dextran, polyethylene glycol, $C_{12}$–$C_{20}$ fatty acids, 2-amino-2-methyl-1-propyl aminomethyl propanol, quaternary ammonium salts, and a salt selected from the group of salts consisting of NaCl, KCl, $CaCl_2$, $MgCl_2$, quaternary ammonium salts, cetyl trimethylammonium bromide, and 4-methoxy-4(3-phosphatidyl choline)spiro(1,2-dioxetane-3-g,l-adamantane) disodium salt;

said surface active agent having a hydrophilic/lipophilic balance value greater than that of said first microcapsule layer-forming compound;

said second microcapsule layer-forming compound having a hydrophilic/lipophilic balance value lower than that of said surface active agent;

creating an interface between said first and second phases in a manner that limits fluid shear to less than about 12 dynes/cm$^2$, and maintains adsorptive surface characteristics at said interface.

38. Microcapsules produced by any of the methods of the preceding claims.

39. The microcapsules of claim 38 wherein said microcapsules are of a uniform distribution of diameters.

40. The microcapsules of claim 39 wherein said diameter distribution is in a range of about 1.0 to 350.0 microns.

41. The microcapsule of claim 38 further comprising at least one nascent crystal of a pharmaceutical composition.

42. The microcapsules of claim 41 wherein said crystal occupies at least about 10 percent of the volume of said microcapsule.

43. A microcapsule produced by the method of claim 37.

44. A multi-layered microcapsule, comprising:

a first layer comprising a first solvent, a first microcapsule layer-forming compound soluble in said first layer and immiscible with a second layer, a co-solvent, oil, and water;

said second layer immiscible with said first layer, said second layer comprising a second solvent, a second microcapsule layer-forming compound soluble in said second layer and immiscible with said first layer, a surface active agent, and a salt;

said surface active agent having a hydrophilic/lipophilic balance value greater than that of said first microcapsule layer-forming compound; and, said second microcapsule layer-forming compound having a hydrophilic/lipophilic balance value lower than that of said surface active agent.

45. The microcapsule of claim 44 wherein said first solvent is organic.

46. The microcapsule of claim 45 wherein said organic solvent is selected from the group of organic solvents consisting of methyl alcohol, ethyl alcohol and isopropyl alcohol.

47. The microcapsule of claim 45 wherein said first microcapsule layer-forming compound is selected from the group consisting of glycerol monosterate, glycerol monooleate, glycerol monolaurate, glycerol dioleate, glycerol distearate, cholesterol, stigmasterol, phytosterol, campesterol, and lecithins.

48. The microcapsule of claim 44 wherein said first solvent is aqueous.

49. The microcapsule of claim 48 wherein said first microcapsule layer-forming compound is selected from the group of microcapsule layerforming compounds consisting of polyvinyl pyrrolidone, polyvinyl alcohols, hydrocolloids, and lecithins.

50. The microcapsule of claim 49 wherein said hydrocolloid is selected from the group of hydrocolloids consisting of gelatin, gum tragacanth, carrageenan, Karaya gum, Guar gum, gum arabic, alginates, carboxymethyl cellulose, hydroxypropyl cellulose, and carboxypropyl cellulose.

51. The microcapsule of claim 44, said first layer further comprising a co-solvent, wherein said co-solvent is selected from the group of co-solvents consisting of $C_3$–$C_8$ alcohols, tetrahydrofuran, dioxane, acetonitrile, dimethylformamide, dimethylacetamide, and dimethyl sulfoxide.

52. The microcapsule of claim 44 wherein said oil is selected from the group of oils consisting of poppy seed oil, olive oil, peanut oil, sesame oil, cotton seed oil, soybean oil, safflower oil, corn oil, sunflower seed oil, canola oil, mineral oil, $C_{20}$–$C_{38}$ paraffinic oil, and liquid petrolatum.

53. The microcapsule of claim 44 wherein said oil is an unsaturated oil which has been halogenated.

54. The microcapsule of claim 44 wherein said second microcapsule layer-forming compound is selected from the group consisting of polyethyleneglycol, dextran, polyvinylpyrrolidone, polyvinyl alcohols, gelatin, gum tragacanth, carrageenan, Karaya gum, Guar gum, gum arabic, alginates, carboxymethyl cellulose, hydroxypropyl cellulose, carboxypropyl cellulose, and lecithins.

55. The microcapsule of claim 44 wherein said surface active agent has a hydrophilic/lipophilic balance value of about 10.0 or greater.

56. The microcapsule of claim 55 wherein said surface active agent is selected from the group of nonionic surface active agents consisting of sorbitan monooleate treated with ethylene oxide, dextran, polyethylene glycol, $C_{12}$–$C_{20}$ fatty acids, 2-amino-2-methyl-1-propyl aminomethyl propanol, amphoteric salts, and quaternary ammonium salts.

57. The microcapsule of claim 44 wherein said salt is selected from the group of salts consisting of NaCl, KCl, $CaCl_2$, $MgCl_2$, quaternary ammonium salts, cetyl trimethylammonium bromide, and 4-methoxy-4(3-phosphatidyl choline)spiro(1,2-dioxetane-3-g,l-adamantane) disodium salt.

58. The microcapsule of claim 44 wherein said first layer further comprises a pharmaceutical composition.

59. The microcapsule of claim 58 wherein said pharmaceutical composition is selected from the group of pharmaceutical compositions consisting of cytotoxins, proteases, cytokines, anti-nauseants, steroids, anti-fungal agents, fibrinolytic enzymes, and antibiotics.

60. The microcapsule of claim 58 wherein said pharmaceutical composition is in suspension.

61. The microcapsule of claim 44 wherein said second layer further comprises a pharmaceutical composition.

62. The microcapsule of claim 61 wherein said pharmaceutical composition is selected from the group of pharmaceutical compositions consisting of cytotoxins, proteases, cytokines, anti-nauseants, steroids, anti-fungal agents, fibrinolytic enzymes, and antibiotics.

63. The microcapsule of claim 61 wherein said pharmaceutical composition is in suspension.

64. The microcapsule of claim 58 or 61 wherein said pharmaceutical is at a concentration sufficient to allow nascent crystal formation within said microcapsule.

65. The microcapsule of claim 44 comprising a third layer, said third layer comprising an oil or paraffin.

66. The microcapsule of claim 65, wherein said third layer further comprises a pharmaceutical composition.

67. The microcapsule of claim 65, wherein said third layer further comprises a surface active agent.

68. The microcapsule of claim 44 comprising a third layer, said third layer comprising an aqueous solution.

69. The microcapsule of claim 68, wherein said third layer further comprises a pharmaceutical composition.

70. The microcapsule of claim 68, wherein said third layer further comprises an adjuvant.

71. The microcapsule of claim 70, wherein said adjuvant further comprises an immunoglobulin, peptide, protein, hydrocolloid or polysaccharide.

72. The microcapsule of claim 71, wherein said peptide or said protein selectively adheres to a target cell, tissue or tumor.

73. The microcapsule of claim 71, wherein said hydrocolloid is selected from the group of such hydrocolloids consisting of collagen, isoelectric gelatin, agar, gum arabic, gum tragacanth, carboxymethylcellulose (CMS), carboxymethyl/ethyl cellulose (CMEC), hydroxyethylcellulose (HEC), hydroxymethyl/ethyl cellulose (HMEC), hydroxypropyl cellulose (HPC), and carrageenans.

74. The microcapsule of claim 68, wherein said third layer further comprises a surface active agent.

75. The microcapsule of claim 44 wherein one or more of said layers further comprise fluorescent molecules selected from the group of fluorescent molecules consisting of fluoresceins, cyanins, naturally fluorescent molecules, and rhodamines.

76. The microcapsule of claim 44 formed under microgravity.

77. The microcapsule of claim 76 wherein said microgravity is at least 1.0 minutes in duration.

78. The microcapsule of claim 44 formed below ambient temperature.

79. The microcapsule of claim 44 comprising layers at least initially substantially balanced as to specific gravity between said layers.

80. A multi-layered microcapsule, comprising:

a first layer comprising an organic solvent selected from the group of organic solvents consisting of methyl alcohol, ethyl alcohol and isopropyl alcohol, a first microcapsule layer-forming compound soluble in said first phase selected from the group consisting of glycerol monosterate, glycerol monooleate, glycerol monolaurate, glycerol dioleate, glycerol distearate, cholesterol, stigmasterol, phytosterol, campesterol, and lecithins, a co-solvent selected from the group of co-solvents consisting of $C_3$–$C_8$ alcohols, tetrahydrofuran, dioxane, acetonitrile, dimethylformamide, dimethylacetamide, and dimethyl sulfoxide, oil selected from the group of oils consisting of poppy seed oil, olive oil, peanut oil, sesame oil, cotton seed oil, soybean oil, safflower oil, corn oil, sunflower seed oil, canola oil, mineral oil, a $C_{20}$–$C_{38}$ paraffinic oil, liquid petrolatum, and water;

a second layer immiscible with said first layer, said second layer comprising water, a second microcapsule layer-forming compound soluble in said second phase selected from the group consisting of polyethyleneglycol, dextran polyvinylpyrrolidone, polyvinyl alcohols, gelatin, gum tragacanth, carrageenan, Karaya gum, Guar gum, gum arabic, alginates, carboxymethyl cellulose, hydroxypropyl cellulose, carboxypropyl cellulose, and lecithins, a surface active agent sorbitan monooleate treated with ethylene oxide, dextran, polyethylene glycol, $C_{12}$–$C_{20}$ fatty acids, 2-amino-2-methyl-1-propyl aminomethyl propanol, amphoteric salts, and quaternary ammonium salts, and a salt selected from the group of salts consisting of NaCl, KCl, $CaCl_2$, $MgCl_2$, quaternary ammonium salts, cetyl trimethylammonium bromide, and 4-methoxy-4(3-phosphatidyl choline)spiro(1,2-dioxetane-3-g,l-adamantane) disodium salt;

said surface active agent having a hydrophilic/lipophilic balance value greater than that of said first microcapsule layer-forming compound; and, said second microcapsule layer-forming compound having a hydrophilic/lipophilic balance value lower than that of said surface active agent.

81. The microcapsule of claim 58 further comprising at least two different pharmaceuticals, a first pharmaceutical in said first phase and a second pharmaceutical in said second phase.

82. The microcapsule of claim 44 further comprising a radiopaque contrast agent.

83. The microcapsule of claim 44 further comprising a magnetic resonance contrast agent.

84. The microcapsule of claim 83 wherein said contrast agent is selected from the group of metallo-organic compounds consisting of ferrous gluconate, Gadolinium diethylenetriamine pentaacetic acid, and iron pentacarbonyl.

* * * * *